US008710067B2

(12) United States Patent
Yamin et al.

(10) Patent No.: US 8,710,067 B2
(45) Date of Patent: *Apr. 29, 2014

(54) METHOD FOR THE TREATMENT, ALLEVIATION OF SYMPTOMS OF, RELIEVING, IMPROVING AND PREVENTING A COGNITIVE DISEASE, DISORDER OR CONDITION

(75) Inventors: Rina Yamin, Rehovot (IL); Dalia Megiddo, M.P. Judean Hills (IL); Yaron Ilan, Jerusalem (IL)

(73) Assignee: Alcobra Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/541,568

(22) Filed: Jul. 3, 2012

(65) Prior Publication Data
US 2013/0012549 A1   Jan. 10, 2013

Related U.S. Application Data

(63) Continuation of application No. 13/380,215, filed as application No. PCT/IL2010/000506 on Jun. 24, 2010.

(60) Provisional application No. 61/220,376, filed on Jun. 25, 2009, provisional application No. 61/305,641, filed on Feb. 18, 2010.

(51) Int. Cl.
| A01N 43/50 | (2006.01) |
| A01N 31/00 | (2006.01) |
| A61K 31/435 | (2006.01) |
| A61K 31/045 | (2006.01) |
| C07D 213/62 | (2006.01) |

(52) U.S. Cl.
USPC ............................ 514/277; 514/738; 546/261

(58) Field of Classification Search
USPC .................................. 514/277, 738; 546/261
See application file for complete search history.

(56) References Cited

U.S. PATENT DOCUMENTS

| 4,313,952 | A | 2/1982 | Baldacci |
| 5,942,530 | A * | 8/1999 | Panetta et al. ................. 514/374 |
| 6,541,043 | B2 | 4/2003 | Lang |
| 2002/0192303 | A1 | 12/2002 | Arver et al. |
| 2003/0147957 | A1* | 8/2003 | Licht et al. ..................... 424/471 |
| 2003/0148992 | A1* | 8/2003 | Block et al. ..................... 514/52 |
| 2004/0162270 | A1 | 8/2004 | Oslick et al. |
| 2005/0271739 | A1 | 12/2005 | Wang |
| 2007/0248696 | A1 | 10/2007 | Maletto et al. |
| 2008/0146577 | A1* | 6/2008 | Matalon et al. ................ 514/249 |
| 2009/0081179 | A1 | 3/2009 | Kiliaan et al. |
| 2010/0256198 | A1 | 10/2010 | Megiddo et al. |
| 2012/0277270 | A1* | 11/2012 | Megiddo et al. .............. 514/345 |

FOREIGN PATENT DOCUMENTS

| CN | 1650862 A | 8/2005 |
| EP | 511943 A2 | 11/1992 |
| FR | 2172906 A1 | 10/1973 |
| GB | 1286161 A | 8/1972 |
| WO | WO-9418965 A1 | 9/1994 |
| WO | WO-03003981 A2 | 1/2003 |
| WO | WO-2005048974 A2 | 6/2005 |
| WO | WO-2008066353 A1 | 6/2008 |
| WO | WO-2009004629 A2 | 1/2009 |
| WO | WO-2010013242 A1 | 2/2010 |

OTHER PUBLICATIONS

Elia et al. "Treatment of Attention-Deficit-Hyperactivity Disorder", The New England Journal of Medicine, 1999, pp. 780-788.*
Lü et al. "Pharmacokinetics of Metadoxine for Injection After Repeated Doses in Healthy Volunteers." *Chinese Med. J.* 120.2(2007):166-168.
"'Metadoxil' Drug Information."*ABC J.* Jul. 7, 1997. (Russian Original and English Translation).
"Alcohol Dependence." *Guidance for Medicine: Diagnostics and Therapy, The Merck Manual.* 2(1997):15. (Russian Original and English Translation).
"Results." *Drug Preparations by Medical Scientific Manufacture Complex Biotica*, Moscow (2002):17, 19, 20, 22, 24. (Russian Original and English Translation).
"Vitamin B6."*Alveda Pharma*. 2001. Web. Feb. 2, 2005. http://www.alvedapharma.com/PDF/PyridoxineEnglish.pdf.
Ajay et al. "Design, Development and in Vitro Evaluation of Metadoxine Microbeads: Ionic Gelation Method." *Pharma. Res.* 5.1(2011):62-69.
Annoni et al. "Pyridoxol L,2-Pyrrolidon-5 Carboxylate Prevents Active Fibroplasia in CCl4-Treated Rats." *Pharm. Res.* 25.1(1992):87-93.
Christie. "Scotland's Drinking Laws Set for Reform to Stem Alcohol Problems." *BMJ.* 327.7413(2003):467.
Felicioli et al. "Effects of Pyridoxine-Pyrrolidon-Carboxylate on Hepatic and Cerebral ATP Levels in Ethanol Treated Rats." *Int. J. Clin. Pharmacol. Ther. Toxicol.* 18.6(1980):277-280. (Abstract Only).
Johansson et al. "Studies on the Metabolism of Labeled Pyridoxine in Man." *Am. J. Clin. Nutr.* 18(1966):185-196.
Morse et al. "The Definition of Alcoholism." *JAMA.* 268. 8(2008):1012-1014.

(Continued)

*Primary Examiner* — Kendra D Carter
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

The present invention provides uses of a salt adduct comprising at least one positively charged moiety being a pyridoxine or a derivative thereof and at least one carboxylated 5- to 7-membered lactam ring, optionally additionally substituted, for the preparation of a medicament for the treatment, alleviation of symptoms of, relieving, improving and preventing a cognitive disease, disorder or condition in a subject. Additionally, the invention provides use of said salt adducts for the preparation of medicaments for the improvement of cognitive functions in a healthy subject.

6 Claims, 2 Drawing Sheets

(56) References Cited

OTHER PUBLICATIONS

Pellegrini-Giampietro et al. "Pyrrolidone Carboxylic Acid in Acute and Chronic Alcoholism." *Recenti Progressi Medicina.* 80.3(1989):160-164.

Pal'tsev et al. "Non-Alcoholic Fatty Liver Disease: Age Peculiarities, Breakthrough in Pathogenic Therapy." *Eksp. Klin. Gastroenterol.* 8(2009):19-25. (English Abstract Only).

Safonova et al. "Metadoxil in the Treatment of Hepatotoxic Action of Cytostatics." *Issues Oncol.* 5(2005):599-600. (Russian Original and English Abstract).

Shpilenya et al. "Metadoxine in Acute Alcohol Intoxication: A Double-Blind, Randomized, Placebo-Controlled Study." *Alcohol Clin. Exp. Res.* 26.3(2002):340-346.

Yifan et al. "Influence of Metadoxine on the Concentration of Ethanol in Blood of Rats With Acute Ethanol Intoxication." *J. Health Toxicol.* 17.2(2003). (English Translation of Summary).

"Efficacy Study of Metadoxine SR Formulation in Attention Deficit Hyperactivity Disorder (ADHD) Subjects (NCT00995085)." *Clinicaltrials.gov* (Oct. 2009).

Addolorato et al. "Metadoxine in the Treatment of Acute nd Chronic Alcoholism: A Review." *Int. J. Immunopath. Pharmacol.* 16.3(2003):207-214.

Antonelli et al. "Pyroglutamic Acid Administration Modifies the Electrocorticogram and Increases the Release of Acetycholine and Gaba From the Guinea-Pig Cerebral Cortex." *Pharmacol. Res. Commun.* 16.2(1984):189-197.

Guerrini et al. "A Follow Up Study on the Efficacy of Metadoxine in the Treatment of Alcohol Dependence." *Subst. Abuse Treat. Prev. Policy.* 1.1(2006):35.

Lalazar et al. "A Novel Slow Release Formulation of Metadoxine Improves Motor and Cognitive Function, Decreases Craving After Alcohol Ingestion in Healthy Volunteers: Results of a Phase I Clinical Trial." *Hepatol.* 50.4(2009):611A. (Abstract #650).

Langer. "New Methods of Drug Delivery." *Science.* 249. 4976(1990):1527-1533.

Lingetti et al. "Treatment of Cerebral Vasculopathies With Metadoxine." *Acta Gerontol.* 30.3(1980):230-234. (English Abstract Only).

Lü et al. "Pharmacokinetics of Metadoxine for Injection After Repeated Doses in Healthy Volunteers." *Chinese Med. J.* 120.2(2007):166-168.

Sinforiani et al. "Effects of Metadoxine (Metadoxil®) on the Early Phase of Cognitive Recovery in Abstinent Alcoholics." *Clin. Trials J.* 27.2(1990):103-111.

Vonghia et al. "Acute Alcohol Intoxication." *Eur. J. Int. Med.* 19.8(2008):561-567.

\* cited by examiner

METHOD FOR THE TREATMENT, ALLEVIATION OF SYMPTOMS OF, RELIEVING, IMPROVING AND PREVENTING A COGNITIVE DISEASE, DISORDER OR CONDITION

RELATED APPLICATIONS

This application is a continuation of U.S. application Ser. No. 13/380,215, filed Mar. 6, 2012, which is a National Stage Entry Application and claims benefit of priority of International Application No. PCT/IL2010/000506, filed on Jun. 24, 2010, which claims benefit of priority under 35 USC §119(e) to U.S. Provisional Application No. 61/220,376, filed Jun. 25, 2009, and from U.S. Provisional Application No. 61/305,641, filed Feb. 18, 2010.

FIELD OF THE INVENTION

The present invention relates to methods of treating and/or relieving and/or improving and/or preventing a cognitive disease, disorder or condition in a subject in need thereof using metadoxine and derivatives thereof or compositions comprising thereof.

BACKGROUND OF THE INVENTION

Alterations in cognitive function may lead to altered state of consciousness, or to altered cognitive function, and may manifest in memory impairment, or learning disabilities, or any type of altered function.

Attention deficit hyperactivity disorder (ADHD) is characterized by pervasive and impairing symptoms of inattention, hyperactivity, and impulsivity. ADHD/ADD is one of the most thoroughly researched disorders in medicine. It has been associated with a broad range of negative outcomes for affected subjects and with serious financial burden to families and society, which marks it as a major public health problem.

Amnesia is a condition which can be defined by loss of memory due to some disturbing or appalling psychological experience, brain injury or chain of emotional events. There are different reasons and causes of amnesia such as organic or functional reasons. Organic amnesia is caused due to damage to the brain by external factors which can be due to physical impacts like trauma or disease. Functional amnesia is due to psychological factors. There are many reasons which can be the cause of amnesia-like phenomena: head injury, severe illness, high fever, seizures, emotional shock or hysteria, alcohol-related brain damage, drugs, stroke, Alzheimer's disease and brain surgery, any type of metabolic disease such as hepatic or uremic encephalopathy, any disease that altered blood flow in the brain, or altered neurotransmission in the brain, or is the result of increase or decrease in any type of metabolite in the brains, any disease associated with accumulation of amyloid in the brain, or with the alteration of electrical function, or metabolic function, or any type of altered mechanism in the brain.

Fatigue is related to most lifestyle habits and mental health conditions. The literature describes fatigue as a complex phenomenon that represents decreased ability to perform or accomplish mental or physical tasks or respond after extended activity as well as decreased motivation to perform tasks. The level of fatigue experienced by an individual relates to past cumulative daily activity patterns and to periods of sleep and activity. In summary, fatigue results from time spent on tasks, natural circadian factors, and inadequate sleep. Alertness, on the other hand, is the state of readiness and attentiveness achieved without artificial or natural enhancements.

Having difficulties with concentrating is a symptom that can arise from both physical and psychological or emotional problems. Symptoms of lack of or deficiency in concentration may or may not be associated with other memory-related symptoms such as forgetfulness. Physical medical conditions that affect concentration include Lyme disease, whiplash, and various others. Psychological conditions that may impair concentration include depression, certain anxiety disorders, and stress. Sleep disorders such as insomnia or sleep apnea can also impair concentration ability.

Metadoxine is a pyridoxine-pyrrolidone carboxylate (also known as pyridoxol L,2-pyrrolidon-5 carboxylate or pyridoxine 5-oxo-2-pyrrolidon-carboxylate) with significant alcohol scavenging properties. Metadoxine has been used to treat acute alcohol intoxication, poisoning, and certain other acute alcohol syndromes (reviewed in Addolorato et al., *Int. J. Immunopathol. Pharmacol.* (2003) 16:207-214). Long term data show that metadoxine is safe for use by humans.

Metadoxine accelerates the elimination of alcohol from the blood and tissues, helping restore the functional structure of the liver and alleviate neuro-psychological disorders associated with chronic alcohol intoxication and related syndromes. In animal studies, metadoxine increased plasma clearance and urinary excretion of ethanol, inhibited the increased production of fatty acid esters in the liver during chronic alcohol intake, reduced oxidative stress and prevented glutathione depletion in hepatic tissues (Antonelli et al., *Pharmacol. Res. Commun.* (1984) 16:189-197). In the brain, metadoxine increased the level of GABA and acetylcholine in the fronto-parietal cortex of guinea pigs.

Metadoxine is an ion-pair between pyrrolidone carboxylate (PCA) and pyridoxine (vitamin B6) with the two compounds linked in a single product by salification. The pairing with PCA synergistically increases the pharmacological activity of pyridoxine (see, e.g., U.S. Pat. No. 4,313,952). Metadoxine is freely soluble in water and in gastric fluid. Oral absorption of the drug is fast with high bioavailability (60-80%). The half life of metadoxine in human serum is short (40-60 minutes) without appreciable differences between oral and intravenous administration (Addolorato et al., supra; Lu Yuan et al., *Chin. Med. J.* 2007 120(2) 160-168).

Metadoxine is marketed in several countries as a prescription drug in the form of 500 mg tablets and 300 mg injections. Tablets contain 500 mg of metadoxine, microcrystalline cellulose and magnesium stearate. Ampoules contain 300 mg of metadoxine, sodium metabisulfite, EDTA sodium, methyl-p-hydroxybenzoate and water.

U.S. Pat. No. 6,541,043 describes a composition and method for treating Attention Deficit/Hyperactivity Disorder (ADHD), the composition comprising dimethylaminoethanol (DMAE), together with a variety of agents, inter alia vitamin B6, optionally with conventional drugs for treating ADHD. WO03/003981 discloses compositions for the structural/functional nutritional support for subjects with poor focus, concentration and/or memory, as well as subjects who subjectively experience transient mental fatigue or poor cognitive function. These compositions comprise, inter alia B-complex vitamins, including B6, and L-pyroglutamic acid, together with a large number of other ingredients. WO09/004,629 describes a method for decreasing or preventing symptoms or effects of alcohol consumption comprising administration metadoxine. US20070248696 describes a composition for improving neuromuscular facilitation, also known as "muscle memory," and enhancing cognitive functions, such as memory and mental focus, in the form of a dietary supplement that comprises, amongst many ingredients, also vitamin B6. US20090081179 discloses the use of polyunsaturated fatty acids and e.g. vitamin B6 amongst others, in treatment of patients suffering from Parkinson's disease, Huntington's chorea, epilepsy, schizophrenia, paranoia, depression, sleep disorders, impaired memory function, psychoses, dementia and ADHD. EP 511943 describes pyroglutamic acid derivatives as enhancers of learning processes and memory. The effect of administration of metadoxine on memory recovery was tested on abstinent chronic alcoholic. Vitamin B6 was administered to a control group of similar patients. It was found that metadoxine helps recovery of short-term memory after 1-2 months of abstinence, and that its effect was superior to that of vitamin B6 [ Sinforiani et al., Clin. Trials J., 27(2):103-111 (1990)]. WO2010/013242 discloses salt adducts comprising at least one positively charged moiety being a pyridoxine or a derivative thereof and at least one carboxylated 5- to 7-membered lactam ring, optionally additionally substituted, methods of their preparation, and pharmaceutical compositions and medicaments comprising them for the treatment of diseases or disorders associated with or inflicted by alcohol consumption.

There exists a need for methods able to treat, alleviate the symptoms of, relieve, improve and prevent a cognitive disease, disorder or condition, cognitive behavior and functioning, and maintain these improvements for prolonged duration.

It is an object of the invention to provide methods for treating such cognitive disorders and deficiencies using metadoxine and derivatives thereof or compositions comprising thereof. It is another object of the invention to provide compositions comprising metadoxine or derivatives thereof, for long-term treatment of cognitive deficiencies. These and other objects of the invention will become apparent as the description proceeds.

SUMMARY OF THE INVENTION

The present invention is intended at solving one or more of the problems referred to above, by providing various methods for improving cognitive performance by administering a composition comprising metadoxine or a derivative thereof to a subject in need. Metadoxine and/or metadoxine derivatives compositions formulated for sustained or controlled release, optionally also including an immediate release component or a metadoxine or a metadoxine derivative, and methods for using such sustained or controlled release or combined metadoxine or metadoxine derivatives formulations of the invention, are also provided. The composition may comprise metadoxine or metadoxine derivative formulated for sustained release or controlled release. In some aspects, the compositions comprising metadoxine or metadoxine derivatives may have a portion of the metadoxine or metadoxine derivatives formulated for sustained or controlled release and a portion of the metadoxine or metadoxine derivatives formulated for immediate release.

In one of its aspect, the invention provides a method for the treatment, alleviation of symptoms of, relieving, improving and preventing a cognitive disease, condition or disorder, in a healthy subject or a patient in need, said method comprising administering to said subject an effective amount of metadoxine or a derivative thereof.

In another aspect the invention provides a method for the treatment, alleviation of symptoms of, relieving, improving and preventing a cognitive disease, disorder or condition in a subject, said method comprising administering to said subject an effective amount of a salt adduct comprising at least one positively charged moiety being a pyridoxine or a derivative thereof and at least one carboxylated 5- to 7-membered lactam ring, optionally additionally substituted.

In a further aspect the invention provides a method for the improvement of cognitive functions in a healthy subject, said method comprising administering to said subject an effective amount of a salt adduct comprising at least one positively charged moiety being a pyridoxine or a derivative thereof and at least one carboxylated 5- to 7-membered lactam ring, optionally additionally substituted.

When referring to "metadoxine", it should be understood to encompass the salt adduct pyridoxine L-2-pyrrolidone-5-carboxylate. Metadoxine is a salt of the corresponding anion of L-2-pyrrolidone-5-carboxylic acid (L-2-pyroglutamic acid) (1) and the protonated derivative of pyridoxine (vitamin B6) (2), having the following structures:

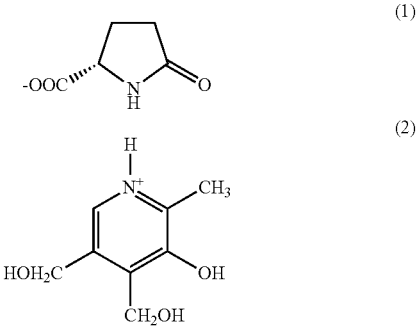

When referring to a "metadoxine derivative" it should be understood to encompass any other salt adduct comprising at least one positively charged moiety being a pyridoxine or a derivative thereof and at least one carboxylated 5- to 7-membered lactam ring, optionally additionally substituted.

In all embodiments of the invention said positively charged moiety is a compound of formula (I):

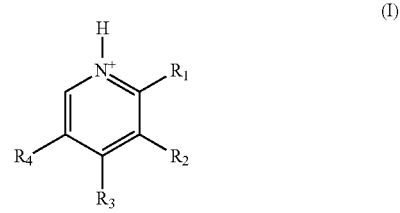

wherein $R_1$ is straight or branched $C_1$-$C_6$ alkyl; $R_2$ is selected from —OH, straight or branched $C_1$-$C_6$ alkoxy, and straight or branched $C_1$-$C_6$ alkoxycarbonyl; $R_3$ and $R_4$ are each independently selected from formyl, straight or branched $C_1$-$C_6$ alkyl optionally substituted by at least one halogen, amine, hydroxy, $C_1$-$C_6$ alkoxy, thiol and $C_1$-$C_6$ alkoxycarbonyl.

In further embodiments of the invention said carboxylated lactam ring is selected from the group consisting of:

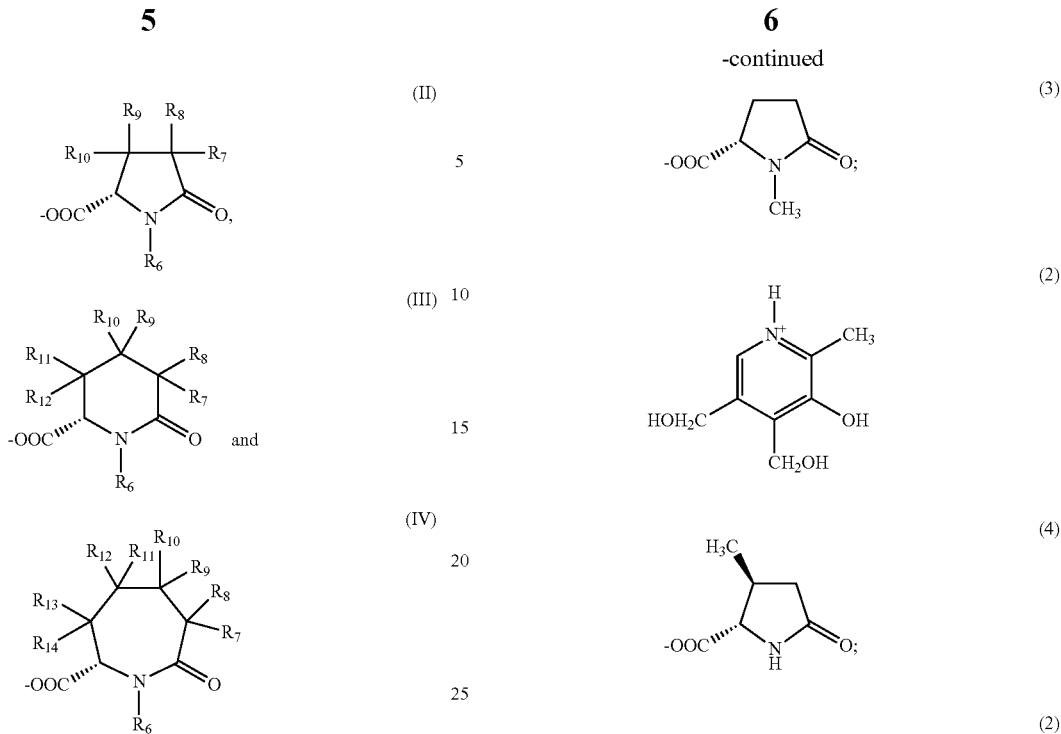

wherein $R_6$ is selected from H, straight or branched $C_1$-$C_6$ alkyl optionally substituted by at least one halogen, straight or branched $C_2$-$C_6$ alkenyl, straight or branched $C_2$-$C_6$ alkynyl, cycloalkyl, aryl and heteroaryl optionally substituted by a $C_1$-$C_6$ alkyl; $R_7$, $R_8$, $R_9$, $R_{10}$ $R_{11}$, $R_{12}$, $R_{13}$ and $R_{14}$ are each independently selected from H, straight or branched $C_1$-$C_6$ alkyl, $C_2$-$C_6$ alkenyl, $C_2$-$C_6$ alkynyl, cycloalkyl, aryl and heteroaryl optionally substituted by at least one group selected from $C_1$-$C_6$ alkyl, halogen, amino, cyano, nitro, thiol, $C_1$-$C_6$ alkoxy, aminocarbonyl, $C_1$-$C_6$ alkoxycarbonyl, $C_1$-$C_6$ carboxyalkyl, $C_1$-$C_6$ alkoxycarbonylalkyl and amidino.

In yet further embodiments of the invention said salt adduct is selected from the following:

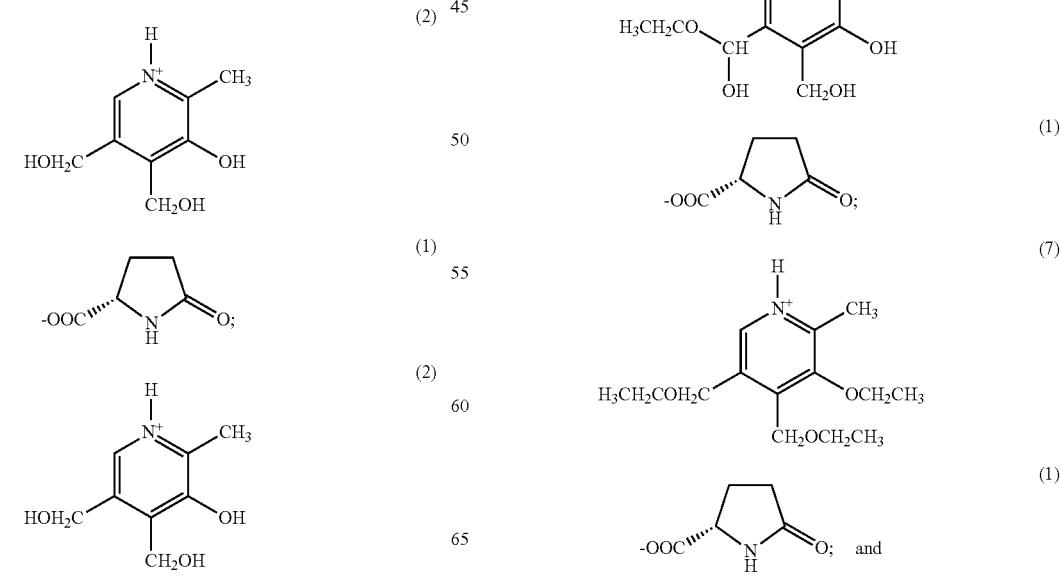

-continued

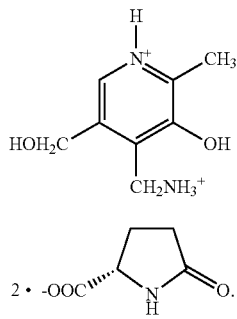
(8)

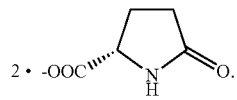
(1)

When referring to a cognitive disease, disorder or condition alleviated, relieved, improved or prevented by a method of the invention, it should be understood to encompass at least one of the following non-limiting conditions: Attention Deficit/Hyperactivity Disorder (ADHD/ADD), impaired memory (Amnesia), impaired wakefulness, mental fatigue conditions (including disease related fatigue), Shift Work Sleep Disorder, Narcolepsy, Obstructive Sleep Apnea/Hypopnea Syndrome, Depression, Substance dependence (including for example addictive substances), Parkinson's disease, Schizophrenia, Poor concentration, and Poor focus, or any combination thereof.

In another one of its aspects, the invention provides a method for the treatment, alleviation of symptoms of, relieving, improving and preventing a neurobehavioral disorder, such as for example ADHD and/or ADD, in a patient in need or in a health subject experiencing symptoms associated with or connected to a permanent or temporary neurobehavioral disorder such as ADHD and/or ADD, said method comprising administering to said subject an effective amount of metadoxine or a derivative thereof.

When referring to a neurobehavioral disorder alleviated, relieved, improved or prevented by a method of the invention, it should be understood to encompass at least one of the following non-limiting conditions: Attention Deficit Disorder (ADD) Attention Deficit Hyperactivity Disorder (ADHD), Poor concentration, and Poor focus, or any combination or symptoms thereof.

The methods of the invention may further improve wakefulness in subjects (at any age, such as for example pediatric, adolescent or adult subjects) who experience excessive sleepiness due to one of the following non-limiting diagnosed sleep disorders: obstructive sleep apnea/hypopnea, shift work sleep disorder and narcolepsy.

Furthermore, a cognitive disease, disorder or condition alleviated, relieved, improved or prevented by a method of the invention may additionally include any condition associated with learning disabilities, impairment of memory, cognitive dysfunction, alteration of cognitive function, including Alzheimer's disease, or any type of encephalopathy, including uremic and hepatic encephalopathy.

In addition, a neurobehavioral disorder alleviated, relieved, improved or prevented by a method of the invention may additionally include any condition associated any symptoms associated or connected with a neurobehavioral disorder such as for example learning disabilities, impairment of memory, cognitive dysfunction, alteration of cognitive function, etc.

Accordingly, in any of the various embodiments of the methods of the invention described above, the composition may comprise metadoxine or metadoxine derivatives formulated for immediate release, sustained release, controlled release, or a combination of any of the foregoing.

When referring to a cognitive function it should be understood to encompass at least one of the following non-limiting list: temporary or long term learning disabilities, temporary or long term impairment of memory, temporary or long term cognitive dysfunction, temporary or long term alteration of cognitive function, temporary or long term concentration impairment, temporary or long term focus impairment, temporary or long term impaired wakefulness, temporary or long term mental fatigue conditions, temporary or long term Shift Work Sleep Disorder, or any combination thereof.

It should be understood that when referring to an improvement in the cognitive functions in a healthy subject, it is meant to encompass any change (minor or significant) in the cognitive condition of a subject. Specifically said improvement may be noticeable in at least one of the following non-limiting list of conditions: temporary or long term learning disabilities, temporary or long term impairment of memory, temporary or long term cognitive dysfunction, temporary or long term alteration of cognitive function, temporary or long term concentration impairment, temporary or long term focus impairment, temporary or long term impaired wakefulness, temporary or long term mental fatigue conditions, temporary or long term Shift Work Sleep Disorder, or any combination thereof.

In certain other aspects, the invention provides a method for increasing the mean $t_{max}$ of metadoxine or metadoxine derivatives in the blood of a subject comprising administering a metadoxine or metadoxine derivatives composition of the invention formulated for sustained release or controlled release, optionally including a portion of the metadoxine or metadoxine derivatives formulated for immediate release.

In certain aspects, the invention provides a use of any one of the compositions of the invention for the manufacture of a therapeutic and/or pharmaceutical composition and/or medicament useful for practicing each of the methods of the invention as described herein, e.g., for treatment, alleviation of symptoms of, relieving, improving and preventing a cognitive disease, disorder or condition in healthy patients or patients suffering from Attention Deficit/Hyperactivity Disorder (ADHD/ADD), impaired memory (Amnesia), mental fatigue conditions, poor concentration, and poor focus. The subject may be a child, an adolescent, an adult or an elderly or aged person.

The invention also relates to any condition associated with learning disabilities, impairment of memory, any alteration of cognitive function, including Alzheimer's disease, related to alterations in blood flow, sclerosis, amyloid deposition, alteration of neurotransmitters in the brain, metabolic alterations such as the accumulation of ammonia, any type of encephalopathy, including uremic and hepatic encephalopathy, or any type of altered functions due to altered levels of any substance.

Alterations in cognitive function may lead to altered state of consciousness, or to altered cognitive function, and may manifest in memory impairment, or learning disabilities, or any type of altered function.

In any of the various embodiments of metadoxine or metadoxine derivatives compositions described herein (e.g., metadoxine or metadoxine derivatives formulated for immediate release, sustained release, controlled release, or a combination of any of the foregoing), the metadoxine may consist of, or comprise a physiologically compatible metadoxine derivative, as described herein.

The invention will be described in more detail on hand of the appended drawings.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
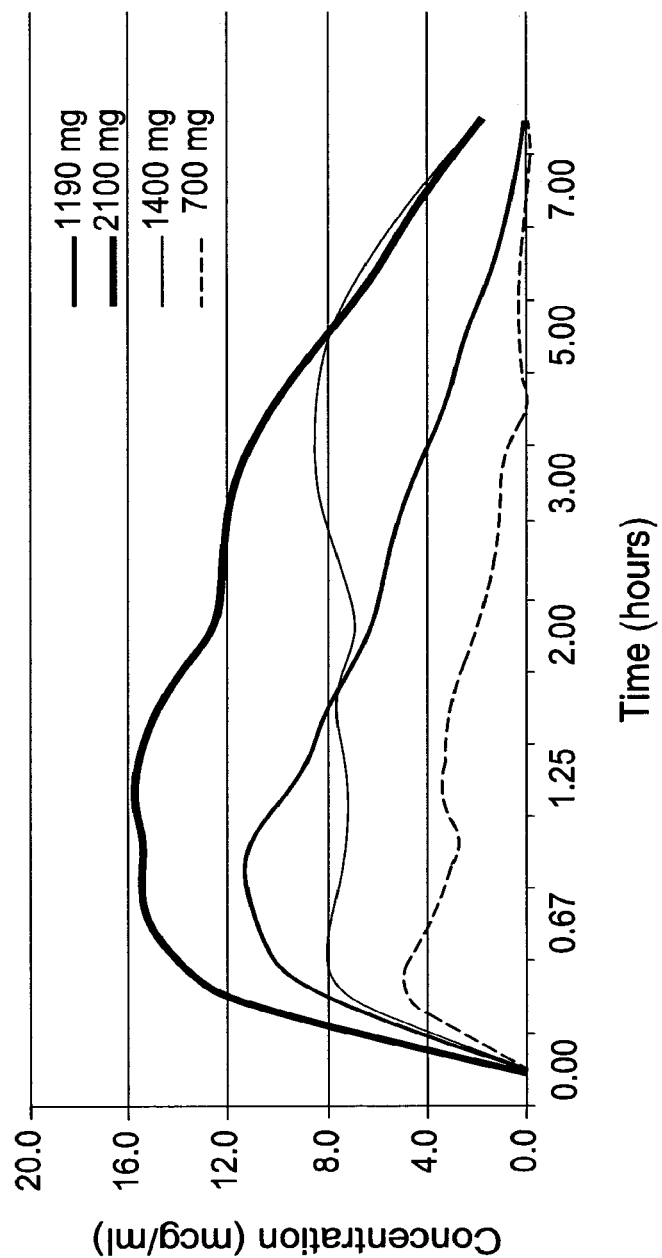
FIG. 1 shows line graphs of release of certain Metadoxine compositions of the present invention as described in Example 1 (Table 3).

In the first aspect the invention provides a method for the treatment, alleviation of symptoms of, relieving, improving and preventing a cognitive disease, disorder or condition in a subject, said method comprising administering to said subject an effective amount of a salt adduct comprising at least one positively charged moiety being a pyridoxine or a derivative thereof and at least one carboxylated 5- to 7-membered lactam ring, optionally additionally substituted.

In a further aspect the invention provides a method for the improvement of cognitive functions in a healthy subject, said method comprising administering to said subject an effective amount of a salt adduct comprising at least one positively charged moiety being a pyridoxine or a derivative thereof and at least one carboxylated 5- to 7-membered lactam ring, optionally additionally substituted.

In another one of its aspects the invention provides, a use of a salt adduct comprising at least one positively charged moiety being a pyridoxine or a derivative thereof and at least one carboxylated 5- to 7-membered lactam ring, optionally additionally substituted, for the preparation of a medicament for the treatment, alleviation of symptoms of, relieving, improving and preventing a cognitive disease, disorder or condition in a subject.

In a further aspect the invention provides, a use of a salt adduct comprising at least one positively charged moiety being a pyridoxine or a derivative thereof and at least one carboxylated 5- to 7-membered lactam ring, optionally additionally, for the preparation of a medicament for the improvement of cognitive functions in a healthy subject.

In all embodiments of the invention said positively charged moiety is a compound of formula (I):

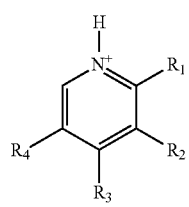

Wherein $R_1$ is straight or branched $C_1$-$C_6$ alkyl; $R_2$ is selected from —OH, straight or branched $C_1$-$C_6$ alkoxy, and straight or branched $C_1$-$C_6$ alkoxycarbonyl; $R_3$ and $R_4$ are each independently selected from formyl, straight or branched $C_1$-$C_6$ alkyl optionally substituted by at least one halogen, amine, hydroxy, $C_1$-$C_6$ alkoxy, thiol and $C_1$-$C_6$ alkoxycarbonyl.

In other embodiments of the invention, said carboxylated lactam ring is selected from the group consisting of:

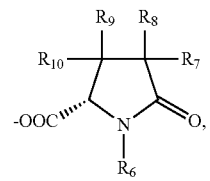

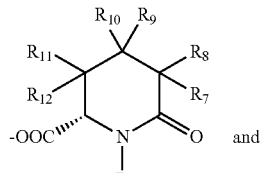

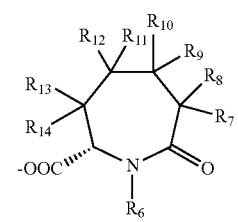

wherein $R_6$ is selected from H, straight or branched $C_1$-$C_6$ alkyl optionally substituted by at least one halogen, straight or branched $C_2$-$C_6$ alkenyl, straight or branched $C_2$-$C_6$ alkynyl, cycloalkyl, aryl and heteroaryl optionally substituted by a $C_1$-$C_6$ alkyl; $R_7$, $R_8$, $R_9$, $R_{10}$, $R_{11}$, $R_{12}$, $R_{13}$ and $R_{14}$ are each independently selected from H, straight or branched $C_1$-$C_6$ alkyl, $C_2$-$C_6$ alkenyl, $C_2$-$C_6$ alkynyl, cycloalkyl, aryl and heteroaryl optionally substituted by at least one group selected from $C_1$-$C_6$ alkyl, halogen, amino, cyano, nitro, thiol, $C_1$-$C_6$ alkoxy, aminocarbonyl, $C_1$-$C_6$ alkoxycarbonyl, $C_1$-$C_6$ carboxyalkyl, $C_1$-$C_6$ alkoxycarbonylalkyl and amidino.

In yet further embodiments of the invention, said carboxylated lactam ring is a compound of formula (II):

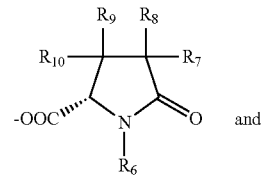

said positively charged moiety is compound (2):

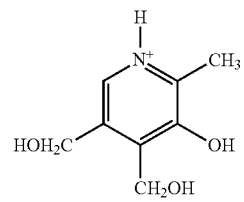

wherein $R_6$, $R_7$, $R_8$, $R_9$ and $R_{10}$ are as defined above.

In other embodiments, said carboxylated lactam ring is compound (1):

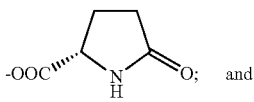 (1)

and said positively charged moiety is a compound of formula (I):

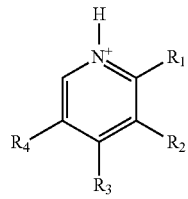 (I)

wherein $R_1$, $R_2$, $R_3$ and $R_4$ are as defined above.

In other embodiments, $R_1$ is a $C_1$-$C_6$ alkyl and $R_2$, $R_3$ and $R_4$ are as defined above.

In further embodiments, $R_2$ is selected from —OH and $C_1$-$C_6$ alkoxy; and $R_1$, $R_3$ and $R_4$ are as defined above.

In further embodiments, $R_3$ is —$CH_2R_{15}$, wherein $R_{15}$ is selected from —$C_1$-$C_6$ alkoxy, —OH and —$NH_3^+$; and $R_1$, $R_2$ and $R_4$ are as defined above.

In other embodiments, $R_4$ is selected from formyl and —$CH_2R_{16}$, wherein $R_{16}$ is selected from —$C_1$-$C_6$ alkoxy and —OH; and $R_1$, $R_2$ and $R_3$ are as defined above.

In further embodiments, $R_1$ is —$CH_3$, $R_2$ is —OH, $R_3$ and $R_4$ are both —$CH_2OH$.

In yet other embodiments, said carboxylated lactam ring is a compound of formula (II):

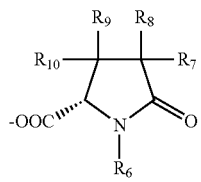 (II)

wherein $R_6$, $R_7$, $R_8$, $R_9$ and $R_{10}$ are as defined above. In some embodiments, $R_6$ is $C_1$-$C_6$ alkyl. In other embodiments, $R_9$ is $C_1$-$C_6$ alkyl.

In further embodiments, said carboxylated lactam ring is a compound of formula (III):

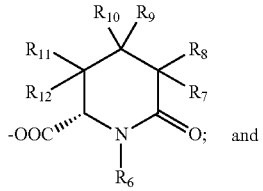 (III)

and said positively charged moiety is a compound of formula (I):

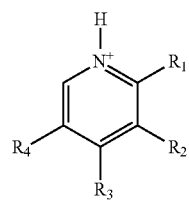 (I)

wherein $R_1$, $R_2$, $R_3$, $R_4$, $R_6$, $R_7$, $R_8$, $R_9$, $R_{10}$, $R_{11}$ and $R_{12}$ are as defined above.

In further embodiments, said carboxylated lactam ring is a compound of formula (IV):

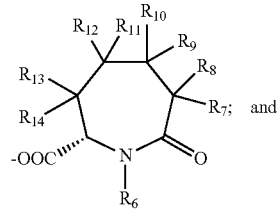 (IV)

and said positively charged moiety is a compound of formula (1):

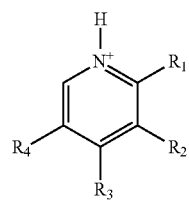 (I)

wherein $R_1$, $R_2$, $R_3$, $R_4$, wherein $R_6$, $R_7$, $R_8$, $R_9$, $R_{10}$, $R_{11}$, $R_{12}$, $R_{13}$ and $R_{14}$ are as defined above.

In yet further embodiments, said positively charged moiety is compound (2):

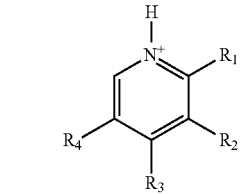 (2)

In some embodiments of the invention, said salt adduct is selected from the following:

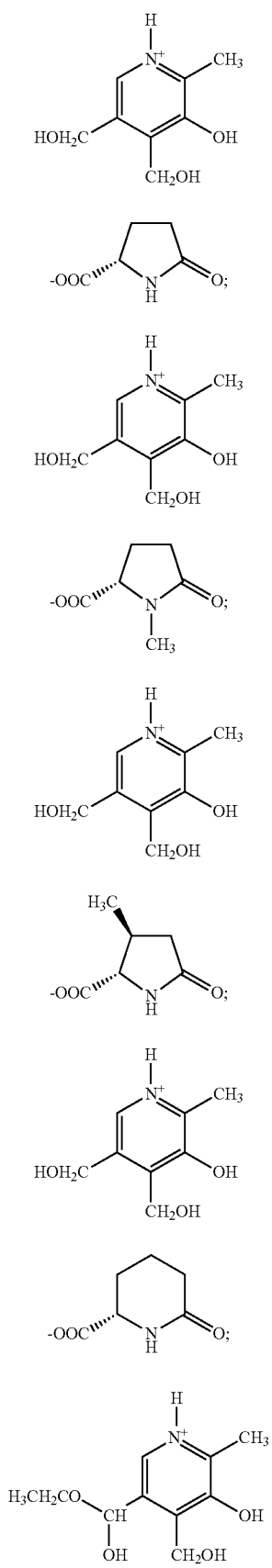

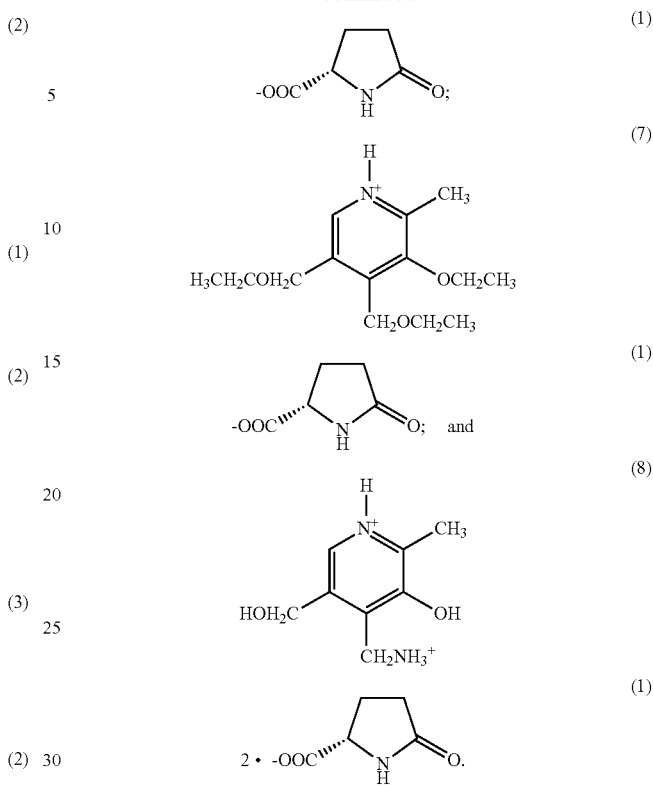

In further embodiments, said cognitive disease, disorder or condition is selected from Attention Deficit/Hyperactivity Disorder (ADHD/ADD), impaired memory (Amnesia), impaired wakefulness, mental fatigue conditions, Shift Work Sleep Disorder, Narcolepsy, Obstructive Sleep Apnea/Hypopnea Syndrome, poor concentration, and poor focus or any combination thereof.

In further embodiments, said cognitive disease, disorder or condition is selected from learning disabilities, impairment of memory, cognitive dysfunction, alteration of cognitive function, including Alzheimer's disease, or any type of encephalopathy, including uremic and hepatic encephalopathy.

In yet further embodiments, said cognitive disease, disorder or condition is a neurobehavioral disease, disorder or condition.

In other embodiments, said neurobehavioral disease, disorder or condition is selected from Attention Deficit Hyperactivity Disorder (ADHD), Attention Deficit Disorder (ADD), impaired memory, poor concentration, and poor focus.

In further embodiments, said cognitive disease, disorder or condition is selected from Attention Deficit Disorder (ADD) or Hyperactivity Disorder (ADHD/ADD), impaired memory (Amnesia), impaired wakefulness, mental fatigue conditions, Shift Work Sleep Disorder, Narcolepsy, Obstructive Sleep Apnea/Hypopnea Syndrome, poor concentration, and poor focus or any combination thereof.

In other embodiments, said cognitive function selected from temporary or long term learning disabilities, temporary or long term impairment of memory, temporary or long term cognitive dysfunction, temporary or long term alteration of cognitive function, temporary or long term concentration impairment, temporary or long term focus impairment, temporary or long term impaired wakefulness, temporary or long term mental fatigue conditions, temporary or long term Shift Work Sleep Disorder, or any combination thereof.

In yet further embodiments, said subject is a child, an adolescent, an adult, or an elderly person.

In all embodiments of the invention, said salt adduct is formulated in a sustained-, delayed or controlled-release dosage form.

In further embodiments of the invention, said salt adduct is formulated in a sustained-, delayed or controlled-release dosage form combined with a salt adduct formulated in an immediate or burst effect dosage form.

In further embodiments of the invention, said salt adduct is formulated to deliver up to 0.1-1000 mg/kg body weight/day of said salt adduct, preferably 1-400 mg/kg body weight of said salt adduct, in a single dose administration or portion thereof. In other embodiments said salt adduct is formulated to deliver up to 100-700 mg/kg body weight/day of said salt adduct.

In other embodiments of the invention, said salt adduct is formulated together with at least one additional pharmaceutically active agent.

In yet further aspects of the invention, there is provided a salt adduct comprising at least one positively charged moiety being a pyridoxine or a derivative thereof and at least one carboxylated 5- to 7-membered lactam ring, optionally additionally substituted, for use in the treatment, alleviation of symptoms of, relieving, improving and preventing a cognitive disease, disorder or condition in a subject.

In another aspect the invention provides, a salt adduct comprising at least one positively charged moiety being a pyridoxine or a derivative thereof and at least one carboxylated 5- to 7-membered lactam ring, optionally additionally, for use in the improvement of cognitive functions in a healthy subject.

DEFINITIONS

For convenience, certain terms employed in the specification, examples, and appended embodiments, are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

The term "prophylactic" or "therapeutic" treatment refers to administration to a subject of one or more of the compositions of the invention. If it is administered prior to clinical manifestation of the unwanted condition (e.g., clinical or other unwanted state of the host animal) then the treatment is prophylactic, i.e., it contributes to prevention of, i.e., protection of the subject against developing an unwanted condition, whereas if administered after manifestation of an unwanted condition, the treatment is therapeutic (i.e., it is intended to diminish, ameliorate or prevent progression of the unwanted condition or side effects there from).

The term "therapeutic effect" refers to a local or systemic effect in animals, particularly mammals, and more particularly humans, caused by a pharmacologically active substance or substances. The term thus means any substance intended for use in diagnosis, cure, mitigation, treatment or prevention of disease or in the enhancement of desirable physical or mental development and conditions in an animal or human. The term "therapeutically effective amount" means that amount of such a substance that produces some desired local or systemic effect at a reasonable benefit/risk ratio applicable to any treatment. In certain embodiments, a therapeutically-effective amount of a compound or composition will depend on its therapeutic index, solubility, and the like. For example, certain metadoxine or metadoxine derivatives formulations of the present invention may be administered in a sufficient amount to produce a reasonable benefit/risk ratio applicable to a selected treatment, as may be determined by the skilled artisan.

The term "effective amount" refers to the amount of a therapeutic reagent that when administered to a subject in an appropriate dose and regimen produces at least one desired result.

A "subject" or "patient" to be treated by a method of the invention may mean either a human or non-human animal, preferably a mammal. The term "subject" as used herein may refer to a healthy individual, or a subject suffering any cognitive problems. The terms "subject" and "healthy subject" and "subject in need" and "patient in need" as used herein exclude subjects under alcohol influence following alcohol consumption of any form, alcoholics (alcohol addicts), and abstinent alcoholics.

The terms "cognitive" or "cognitive function" or "cognitive problems" or cognitive disorders" or "cognitive malfunction" or "cognitive disease, disorder or condition" and the like, may be used herein interchangeably and as used herein may be taken to mean any function of cognition, including but not limited to Attention Deficit/Hyperactivity Disorder (ADHD/ADD), impaired memory (Amnesia), mental fatigue conditions, poor concentration, poor focus, as well as in any condition associated with learning disabilities, impairment of memory, any alteration of cognitive function, including Alzheimer's disease, related to alterations in blood flow, sclerosis, amyloid deposition, alteration of neurotransmitters in the brain, metabolic alterations such as the accumulation of ammonia, any type of encephalopathy, including uremic and hepatic encephalopathy, or any type of altered functions due to altered levels of any substance.

In this connection it may be mentioned that cognitive dysfunction includes any conditions resulting from, inter alia, altered blood flow to whole or part of the brain such as in stroke; altered acid base balance; altered in electrolytes; alteration (increase or decrease) of the level of any metabolite, e.g. urea or ammonia; deposition of any substrate such as amyloid in any part of the brain such as in Alzheimer Disease or Parkinson's Disease; alteration in any part of the immune system whether peripheral or central, that affect the brain, such as in multiple sclerosis or different types of lupus erythematosus; changes in level or function of any cytokine or chemokine; effect/s of drug/s directed towards or targeted to the brain, or affecting the brain in a indirect manner; alterations in neurotransmitters; and any alterations of nerves or synapses in the brain.

The terms "neurobehavioral" or "neurobehavioral function" or "neurobehavioral problems" or "neurobehavioral disorders" or "neurobehavioral malfunction" and the like, may be used herein interchangeably and as used herein may be taken to mean any function of cognition, including but not limited to Attention Deficit/Hyperactivity Disorder (ADHD/ADD), impaired memory, poor concentration, poor focus, as well as in any condition associated with learning disabilities, impairment of memory, or any symptoms associated or connected there from such as for example poor performance in social (home, community, etc.), educational (class, playground, etc.) environments.

The present invention relates to any of the known ADHD subtypes:

(i) Predominantly hyperactive-impulsive: for which most symptoms are in the hyperactivity-impulsivity categories, and some symptoms of inattention are present, although inattention may still be present to some degree, (ii) Predominantly inattentive: the majority of symptoms are in the inattention category and fewer symptoms of hyperactivity-impulsivity are present, although hyperactivity-impulsivity may still be present to some degree; Children with this subtype are less likely to act out or have difficulties getting along with other children. They may sit quietly, but they are not paying attention to what they are doing. Therefore, the child may be overlooked, and parents and teachers may not notice symptoms of ADHD.

(iii) Combined hyperactive-impulsive and inattentive: some of the symptoms of inattention and some symptoms of hyperactivity-impulsivity are present.

Inattentive type symptoms may include:
Subjects may be easily distracted, miss details, forget things, and frequently switch from one activity to another
Subjects may have difficulty focusing on one thing
Subjects may become bored with a task after only a few minutes, unless doing something enjoyable
Subjects may have difficulty focusing attention on organizing and completing a task or learning something new
Subjects may have trouble completing or turning in homework assignments, often losing objects (e.g., pencils, toys, assignments) needed to complete tasks or activities
Subjects do not seem to listen when spoken to
Subjects may daydream, become easily confused, and move slowly
Subjects may have difficulty processing information as quickly and accurately as others
Subjects may struggle to follow instructions.

Predominantly hyperactive-impulsive type symptoms include:
Subjects may be fidget and squirm in their seats
Subjects may talk nonstop
Subjects may dash around, touching or playing with anything and everything in sight
Subjects may have trouble sitting still during dinner, school, and story time
Subjects may be constantly in motion
Subjects may have difficulty doing quiet tasks or activities.

Additional manifestations of primarily impulsivity may include:
Subjects may be very impatient
Subjects may be blurt out inappropriate comments, show their emotions without restraint, and act without regard for consequences
Subjects may have difficulty waiting for things they want or waiting their turns in games As used herein the term "salt adduct" is meant to encompass a salt product of a direct addition of two or more distinct ions, wherein the overall charge of the salt adduct is zero. In certain embodiments, the salt adduct comprises one positively charged moiety having a single positive charge functional group (i.e., the positively charged moiety is charged with +1 net charge) and one negatively charged moiety having a single negative charge functional group (i.e., the negatively charged moiety is charged with −1 net charge). In certain embodiments, the salt adduct comprises one positively charged moiety having two positively charged functional groups, which may be the same or different (i.e., the positively charged moiety is charged with +2 net charge) and two negatively charged moieties, which may be the same or different, and each having a single negative charged functional group (i.e., each negatively charged moiety is charged with −1 net charge). In certain embodiments, the salt adduct comprises two positively charged moieties, which may be the same or different, having each one positively charged functional group (i.e., each positively charged moiety is charged with +1 net charge) and one negatively charged moiety, having two negatively charged functional groups, being the same or different (i.e., the negatively charged moiety is charged with −2 net charge). In certain embodiments, the salt adduct comprises a positively charged moiety charged with +n net charge (originating from one or more positively charged functional groups, which may be the same or different), and a negatively charge moiety having −n (originating from one or more negatively charged functional groups, which may be the same or different) net charge, wherein n is an integer which may be equal to 1, 2, 3, 4, 5 or 6.

As used herein, a "positively charged moiety of a salt adduct" of the invention is the corresponding acid of pyridoxine, or any derivative thereof. In certain embodiments, the positive charge of the positively charged moiety stems from the protonated basic nitrogen atom of pyridoxine (as for example in compound (2)) or any derivative thereof (such as for example compounds of formula (I)). In certain embodiments, the positively charged pyridoxine derivative is substituted with a positively charged functional group such as for example $-NH_3^+$, $-CH_2NH_3^+$, $-NH_2R^+$, $-NHR_2^+$ (wherein each R is independently a $C_1$-$C_6$ alkyl), which may, in some embodiments, be present in addition to the positively charged protonated basic aromatic nitrogen atom in the pyridine ring.

As used herein, a "carboxylated 5- to 7-membered lactam ring" of a salt adduct of the invention, is meant to encompass a γ-lactam, δ-lactam or ε-lactam rings, having a negatively charged carboxylate group ($-COO^-$) substituted thereto. In certain embodiments, said carboxylate group is substituted at the lactam ring carbon atom adjacent to the amide nitrogen. In another embodiment said carboxylated lactam ring is a L-2-pyrrolidone-5-carboxylate (compound (1)). In other embodiments said carboxylate group is substituted on any position of the lactam ring. In certain embodiments, said carboxylated 5- to 7-membered lactam ring may be substituted by another substituent at any position on the lactam ring. The term "halogen" as used herein means F, Cl, Br or I.

The term "$C_1$-$C_6$ alkyl" as used herein represents a saturated, branched or straight hydrocarbon chain having 1, 2, 3, 4, 5 or 6 carbon atoms. Typical $C_{1-6}$ alkyl groups include, but are not limited to, methyl, ethyl, n-propyl, isopropyl, butyl, isobutyl, sec-butyl, tert-butyl, pentyl, isopentyl, hexyl, isohexyl and the like.

The term "$C_2$-$C_6$ alkenyl" as used herein represents a branched or straight hydrocarbon chain having 2, 3, 4, 5 or 6 carbon atoms and at least one double bond positioned between any two carbons of the chain. Examples of such groups include, but are not limited to, ethenyl, 1-propenyl, 2-propenyl, isopropenyl, 1,3-butadienyl, 1-butenyl, 2-butenyl, 1-pentenyl, 2-pentenyl, 1-hexenyl, 2-hexenyl and the like.

The term "$C_2$-$C_6$ alkynyl" as used herein represents a branched or straight hydrocarbon chain having 2, 3, 4, 5 or 6 carbon atoms and at least one triple bond positioned between any two carbons of the chain. Examples of such groups include, but are not limited to, ethynyl, 1-propynyl, 2-propynyl, 1-butynyl, 2-butynyl, 1-pentynyl, 2-pentynyl, 1-hexynyl, 2-hexynyl and the like.

The term "$C_1$-$C_6$ alkoxy" as used herein refers to the radical —O—$C_{1-6}$ alkyl, wherein $C_{1-6}$ alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "$C_1$-$C_6$ alkylthio" as used herein refers to the radical —S—$C_{1-6}$ alkyl, wherein $C_{1-6}$ alkyl is as defined above. Representative examples are methylthio, ethylthio, isopropylthio, n-propylthio, butylthio, pentylthio and the like.

The term "cycloalkyl" as used herein represents a monocyclic, carbocyclic group having 3, 4, 5, 6, 7 or 8 carbon atoms, but may also include heteroatoms such as N, O and/or S. Representative examples are cyclopropyl, cyclobutyl, cyclopentyl, cyclohexyl, cycloheptyl, cyclooctyl and the like.

The term "aryl" as used herein is intended to include carbocyclic aromatic ring systems such as phenyl, biphenylyl, naphthyl, anthracenyl, phenanthrenyl, fluorenyl, indenyl, pentalenyl, azulenyl and the like. Aryl is also intended to include the partially hydrogenated derivatives of the carbocyclic systems enumerated above. Non-limiting examples of such partially hydrogenated derivatives are 1,2,3,4-tetrahydronaphthyl, 1,4-dihydronaphthyl and the like.

The term "heteroaryl" as used herein refers to ring systems in which at least one ring is an aromatic ring in which at least one atom is a non-carbon atom, either substituted or non-substituted, where the non-carbon atom may be, for example, a nitrogen, sulfur or oxygen atom.

The term "$C_1$-$C_6$ alkoxycarbonyl" as used herein refers to the radical —C(O)O—$C_{1-6}$ alkyl, wherein $C_{1-6}$ alkyl is as defined above.

The terms "$C_1$-$C_6$ alkoxy" and "$C_1$-$C_6$ alkylthio" as used herein refers to the radicals $C_{1-6}$—O— and $C_{1-6}$—S—, respectively, wherein $C_{1-6}$ alkyl is as defined above.

The term "hydroxyl" as used herein refers to the radical —OH. As used herein the term "thiol" refers to the radical —SH. As used herein the term "formyl" refers to the radical —COH. As used herein the term "cyano" refers to the radical —CN. As used herein the term "nitro" refers to the radical —$NO_2$.

The term "amine" as used herein refers to —$NH_3$ or any primary (—$NH_2R$), secondary (—$NHR_2$), tertiary (—$NR_3$) or quarternary amines (—$NR_4^+$), wherein each R may be the same or different and independently selected from H, $C_1$-$C_6$ alkyl, $C_1$-$C_6$ alkenyl, $C_1$-$C_6$ alkynyl as defined herein above.

The term "$C_1$-$C_6$ carboxyalkyl" as used herein refers to the radical —CO—($C_1$-$C_6$ alkyl), wherein $C_{1-6}$ alkyl is as defined above.

The term "aminocarbonyl" as used herein refers to the radical —$CONR_2$, wherein each of groups R is independently selected from H, $C_1$-$C_6$ alkyl, $C_1$-$C_6$ alkenyl, $C_1$-$C_6$ alkynyl as defined herein above.

The term "alkoxycarbonylalkyl" as used herein refers to the radical —OCO—($C_1$-$C_6$alkyl), wherein $C_{1-6}$ alkyl is as defined above.

The term "amidino" as used herein refers to the radical —C(=NH)—$NH_2$.

The term "optionally substituted" as used herein means that the moieties referred to are either unsubstituted or substituted with one or more of the substituents specified. When the moieties referred to are substituted with more than one substituent the substituents may be the same or different.

Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety.

It should be understood that moieties of a salt adduct of the invention may contain each at least one chiral center, and thus may exist in, and be isolated as, any stereoisomer thereof including, enantiomers, diastereomers or any mixtures thereof including, but not limited to racemic mixtures. The present invention includes any possible stereoisomer (e.g. enantiomers, diastereomers), any mixtures thereof including, but not limited to, racemic mixtures, of any of the individual moieties of a salt adduct of the invention. Where the herein-described processes for the preparation of each of the moieties of a salt adduct of the invention give rise to mixtures of stereoisomers, these isomers may be separated by conventional techniques, such as preparative chromatography. The moieties of a salt adduct of the invention may be each prepared in any mixture of possible stereoisomers thereof, including but not limited to racemic mixtures thereof, or individual stereoisomers (e.g. enantiomers, diastereomers) may be prepared either by enantiospecific synthesis or by chiral chromatographic separation of a racemate. Whenever referring to amino acids, the invention should be understood to encompass natural and non-natural amino acids or any derivative thereof.

The term "non-natural amino acid" as used herein refers herein to amino acids, or any derivative thereof, that are not among the amino acids which are the building blocks of proteins having L as well as D-configurations, while "natural amino acids", refer to amino acids or any derivative thereof, which are the building blocks of proteins, having L as well as D-configurations.

Table 1 depicts several examples of salt adducts of the present invention.

TABLE 1

| Structural formula | Salt No. |
|---|---|
| [chemical structure with pyridinium ring bearing CH₃, OH, HOCH₂, CH₂NH₃⁺ substituents, paired with 2 equivalents of pyroglutamate anion] | IId |
| [chemical structure with pyridinium ring bearing CH₃, OH, CH₃CH₂O—CH(OH)—, CH₂OH substituents, paired with pyroglutamate anion] | IIe |

TABLE 1-continued

| Structural formula | Salt No. |
|---|---|
| (structure) | IIId |
| (structure) | IIa |
| (structure) | IIb |
| (structure) | IIc |

Throughout this specification, the word "comprise" or variations such as "comprises" or "comprising" will be understood to imply the inclusion of a stated integer or groups of integers but not the exclusion of any other integer or group of integers.

The term "bio-available" means that at least some amount of a particular compound is present in the systemic circulation. Formal calculations of oral bioavailability are described in terms of an F value ("Fundamentals of Clinical Pharmacokinetics," John G. Wegner, Drug Intelligence Publications; Hamilton, Ill. 1975). F values are derived from the ratio of the concentration of the parent drug in the systemic circulation (e.g., plasma) following intravenous administration to the concentration of the parent drug in the systemic circulation after administration by a non-intravenous route (e.g., oral). Therefore, oral bioavailability within the scope of the present invention contemplates the ratio or F value of the amount of parent drug detectable in the plasma after oral administration compared to intravenous administration.

The term "treating" or "treatment" refers to mitigating, improving, relieving or alleviating at least on symptom of a condition, disease or disorder in a mammal, such as a human, or the improvement of an ascertainable measurement associated with a condition, disease or disorder. Treatment as used herein also encompasses treatment of healthy individuals.

The term "acceptable derivative" with respect to metadoxine or metadoxine derivatives refers to any salt, conjugate, ester, complex or other chemical derivative of metadoxine or any of the moieties comprising the same, which, upon administration to a subject, is capable of providing (directly or indirectly) metadoxine or a metabolite or functional residue thereof, or measurable metadoxine activity. The term "physiologically compatible metadoxine derivative" may be used interchangeably herein with the term "acceptable derivative" and refers to a functional, active, pharmaceutically acceptable derivative of metadoxine.

The term "excipient" refers to an inactive substance used as a carrier for the active ingredient in a formulation.

The term "controlled release" refers to any formulation which delivers an agent at a controlled rate for an extended time and is designed to achieve a desired agent level profile.

The term "sustained release" is used in its conventional sense to refer to a formulation that provides for gradual release of an active material over an extended period of time, which in certain embodiments may also further result in substantially constant blood levels over an extended time period, i.e., controlled release.

The term "immediate release" is used in its conventional sense to refer to a formulation that provides for non delayed or controlled release of an active material upon administration.

The term "half-life" of a substance is the time it takes for a substance to lose half of its pharmacologic, physiologic, or other activity. Biological half-life is an important pharmacokinetic parameter and is usually denoted by the abbreviation $t_{1/2}$.

The term "non-invasive" refers to modes of treatment which do not puncture the skin.

The term "non-chronic administration" may be used interchangeably herein with the term "acute administration" and refers to giving a measured or non-measured quantity or portion of a medication to a subject on a non-regular basis. Non-chronic administration may be a single dose treatment or a multiple dose treatment, and may optionally be given over time. Typically but not always, a non-chronic administration is given to treat or prevent a non-chronic condition. Certain chronic conditions may also benefit from non-chronic administration of a metadoxine or metadoxine derivatives composition described herein.

The term "chronic administration" refers to giving a measured quantity of a medication on a regular basis to a subject. In some embodiments, chronic administration is to treat or prevent one or more chronic conditions, problems or diseases. Chronic diseases have one or more of the following characteristics: they are permanent, leave residual disability, are caused by nonreversible pathological alteration, require special training of the patient for rehabilitation, or may be expected to require a long period of supervision, observation, or care.

The term "single dose treatment" refers to giving a measured quantity of a medication to be taken at one time. It is given to treat non-chronic conditions on an irregular basis, depending on personal need.

The term "$t_{max}$" refers to the time to peak concentration. Calculation of time at which maximum concentration occurs after a single dose administration is performed according to the formula:

$$t_{max} = \frac{2.303}{\lambda_\alpha - \lambda_z} \log \frac{\lambda_\alpha}{\lambda_z}$$

where $\lambda_\alpha$ and $\lambda_z$ are the apparent absorption and elimination rate constants, respectively.

Methods of Treatment and Prevention Using Metadoxine or Metadoxine Derivatives Compositions In certain embodiments, the present invention provides a method for improvement of cognitive function and/or behavior in healthy patients or patients suffering from Attention Deficit/Hyperactivity Disorder (ADHD/ADD), impaired memory (Amnesia), mental fatigue conditions, poor concentration, and poor focus comprising administering a composition comprising metadoxine or a derivative thereof. In certain such embodiments, the method comprises non-chronic administration of a composition comprising metadoxine or a derivative thereof.

In certain embodiments, the present invention provides a method for increasing the mean $t_{max}$ of metadoxine or metadoxine derivatives in the blood of a subject for improving or treating cognitive condition as herein defined, comprising administering a composition comprising metadoxine or a derivative thereof, and especially wherein the composition comprises metadoxine or a derivative thereof formulated in whole or in part for sustained or controlled release. In certain such embodiments, the method comprises non-chronic administration of a composition comprising metadoxine or a derivative thereof formulated in whole or in part for sustained or controlled release. In certain embodiments of the invention, the mean $t_{max}$ of metadoxine or metadoxine derivative in the blood of a subject is increased by 50%, 100%, 150%, 200%, 300%, 400%, 500% or greater than 500%.

In certain embodiments, the application provides a method for increasing the half-life ($t_{1/2}$) of metadoxine or a metadoxine derivative in the blood or serum of a subject, for improving or treating cognitive condition as herein defined, comprising administering a composition comprising metadoxine or a derivative thereof, and especially wherein the composition comprises metadoxine or a derivative thereof formulated in whole or in part for sustained release or controlled release, optionally including a portion of the metadoxine or a metadoxine derivative formulated for immediate release. In certain embodiments of the invention, the $t_{1/2}$ of metadoxine or metadoxine derivative in the blood or serum of a subject is increased by 50%, 100%, 150%, 200%, 300%, 400%, 500% or greater than 500%.

In certain of the above described methods of the invention, the metadoxine or derivative thereof may be formulated for immediate release upon administration to the subject. In certain of the above described methods of the invention, the metadoxine or derivative thereof may be formulated for sustained and/or controlled release, and may optionally be formulated to have both immediate release and sustained and/or controlled release characteristics upon administration to the subject. In certain embodiments, metadoxine or a derivative thereof is formulated for non-chronic administration. Metadoxine or metadoxine derivative formulations used by the invention are described in more detail below.

Metadoxine or Metadoxine Derivatives Formulations and Administration Regimens

In certain embodiments, the present invention provides a composition comprising metadoxine or a derivative thereof formulated for sustained and/or controlled release when administered to a subject for improving or treating cognitive condition as herein defined for improving or treating cognitive condition as herein defined.

In certain embodiments, the present invention provides a composition comprising metadoxine or a derivative thereof wherein a portion of the metadoxine or derivative is formulated for sustained and/or controlled release and a portion of the metadoxine or derivative is formulated for immediate release when administered to a subject for improving or treating cognitive condition as herein defined.

In certain embodiments, effective serum levels of the active ingredient are achieved within from about 10 to about 20 or 30 or 40 or 50 or 60, 90 minutes, 2 h, 3 h, 4 h, 5 h, 6 h, 7 h, 8 h, 9 h, 10 h following metadoxine or metadoxine derivative administration. In certain embodiments, effective serum levels of the active ingredient in said subject are achieved within from about 5 to about 20 or 30 or 40 or 50 or 60, 90 minutes, 2 h, 3 h, 4 h, 5 h, 6 h, 7 h, 8 h, 9 h, 10 h following metadoxine or metadoxine derivative administration. In certain embodiments, effective serum levels of the active ingredient are achieved within from about 20 to about 20 or 30 or 40 or 50 or 60, 90 minutes, 2 h, 3 h, 4 h, 5 h, 6 h, 7 h, 8 h, 9 h, 10 h following metadoxine or metadoxine derivative administration. In certain embodiments, effective serum levels of the active ingredient are achieved within about 5, 10, 15, 20, 30, 40, 50 or 60, 90 minutes, 2 h, 3 h, 4 h, 5 h, 6 h, 7 h, 8 h, 9 h, 10 h.

The present inventors have developed innovative approaches for the administration of metadoxine or metadoxine derivative based on enteral (via the digestive tract) and/or parenteral (other routes than digestive tract) routes (WO2009/004629). These approaches provide for a rational design of delivery systems with desired properties based on the meticulous selection of the carrier, e.g. appropriate surfactants/co-surfactants composition or micro/nano particles (such as liposomes or nano-liposomes) entrapping the active ingredients, or other additives or excipients, for the delivery system of interest.

The enteral delivery systems may be designed for oral administration (tablets, sachets, lozenges, capsules, gelcaps, drops, or other palatable form) or rectal administration (suppository or (mini) enema form).

In addition, the delivery system of interest may be in liquid form, for example a drop solution, syrup. Furthermore, the delivery system of interest may be in form of a beverage or food article. Thus, the active ingredient/s used by the invention may be comprised in a beverage, particularly soft drinks like juices, nectars, water, sparkling water and other sparkling drinks, shakes, milk shakes and other milk-based drinks, and the like. Liquid preparations may also be in the form of concentrated syrups, for diluting with water or sparkling water. Alternatively, the active ingredient/s may be comprised in food articles, such as snack bars, health bars, biscuits, cookies, sweets, confectionery products, ice creams, ice lollies, and the like.

Still further, the delivery system may be a food or beverage article comprising a physiologically active pyridoxine derivative, particularly pyridoxol L,2-pyrrolidon-5 carboxylate (metadoxine). In certain embodiments, consumption of the food or beverage article of the invention may lead to achievement of serum levels of the active ingredient within from about 10 to about 40-60 minutes following consumption thereof. Examples may be sweets, chocolate, candies and candy bars, energy bars, ice creams, pastry products and the like.

The parenteral ways of administration include subcutaneous, transferal (diffusion through the intact skin), transmucosal (diffusion through a mucous membrane), sublingual, buccal (absorbed through cheek near gumline) administration, or administration by inhalation. In certain embodiments, the compositions used by the invention are not administered by invasive modes of treatment (i.e., are non-invasive). In certain embodiments, the metadoxine or metadoxine derivative compositions are not administered by intravenous injection.

In certain embodiments, compositions used by the invention are delivered as a microcrystalline powder or a solution suitable for nebulization; for intravaginal or intrarectal administration, pessaries, suppositories, creams or foams. A preferred formulation is a formulation for oral administration. Another preferred formulation is for topical administration. Another preferred formulation is for transmucosal administration, sublingual, buccal (absorbed through cheek near gumline) administration, administration by inhalation or ocular administration, e.g., in eye drops.

Administration of metadoxine or metadoxine derivative for medical uses requires safe and efficient delivery systems. The present invention provides delivery systems for safe delivery of a variety of substances due to their special physico-chemical features, particularly direct absorption, by non-invasive means, and consequent avoidance of side effects. The delivery systems significantly enhance efficiency and quality of metadoxine or metadoxine derivative absorption based on its unique physicochemical features, which enables lower concentrations or amounts of active substance to be delivered to a subject in a biologically active form. The delivery systems of the invention provide for the direct access of the active substance to the tissues and thus provide immediate or near-immediate effects of metadoxine or metadoxine derivative to the treated subject.

Accordingly, in certain embodiments, the present invention uses a non-invasive pharmaceutical delivery system for the improved administration of a physiologically active pyridoxine, particularly pyridoxol L,2-pyrrolidon-5 carboxylate (metadoxine), or a physiologically acceptable derivative thereof, comprising as the active ingredient said physiologically active pyridoxine in a suitable carrier. In certain embodiments, serum levels of the active ingredient are achieved within from about 10 to about 40-60 minutes following administration.

In another embodiment, the invention employs a non-invasive pharmaceutical delivery system for the improved administration of a physiologically active pyridoxine derivative, particularly pyridoxol L,2-pyrrolidon-5 carboxylate (metadoxine), for use in improvement of cognitive behavior in a subject in need thereof, comprising as the active ingredient said pyridoxine derivative, in a suitable carrier. In certain embodiments, serum levels of said active ingredient are achieved within from about 10 to about 40-60 minutes following administration.

In certain embodiments, the drug delivery systems employed by the invention may be designed for oral, nasal, ocular, rectal, subcutaneous, transferal, transmucosal, sublingual, buccal or inhalation administration. The drug delivery systems may provide the active substance in a controlled release mode. In certain embodiments, the drug delivery systems of the invention may further comprise at least one additional pharmaceutically active agent.

The delivery systems used by the invention may generally comprise a buffering agent, an agent that adjusts the osmolarity thereof, and optionally, one or more pharmaceutically acceptable carriers, excipients and/or additives as known in the art. Supplementary pharmaceutically acceptable active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutically active substances is well known in the art.

Except as any conventional media or agent is incompatible with the active ingredient, its use in the therapeutic composition is contemplated. It is contemplated that the active agent can be delivered by any pharmaceutically acceptable route and in any pharmaceutically acceptable dosage form.

Oral forms include, but are not limited to, tablets, capsules, pills, sachets, lozenges, drops, powders, granules, elixirs, tinctures, suspensions, syrups, and emulsions. Also included are oral rapid-release, time controlled-release, and delayed-release pharmaceutical dosage forms. The active drug components can be administered in a single dosage form or in separate dosage forms to be administered together or independently. The active drug components can be administered in a mixture with suitable pharmaceutical diluents, excipients or carriers (collectively referred to herein as "carrier"), materials suitably selected with respect to the intended form of administration.

Where the delivery system is for oral administration and is in the form of a tablet or capsule or the like, the active drug components can be combined with a non-toxic pharmaceutically acceptable inert carrier such as lactose, starch, sucrose, glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate and the like. For oral administration in liquid form, the active drug components can be combined with non-toxic pharmaceutically acceptable inert carriers such as ethanol, glycerol, water and the like. When desired or required, suitable binders, lubricants, disintegrating agents and coloring and flavoring agents can also be incorporated into the mixture. Stabilizing agents such as antioxidants, propyl gallate, sodium ascorbate, citric acid, calcium metabisulphite, hydroquinone, and 7-hydroxycoumarin can also be added to stabilize the dosage forms. Other suitable compounds can include gelatin, sweeteners, natural and synthetic gums such as acacia, tragacanth, or alginates, carboxymethylcellulose, polyethylene, glycol, waxes and the like.

Additional suitable pharmaceutically acceptable carriers that may be used in these pharmaceutical compositions include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. In some embodiments, the pharmaceutically acceptable carrier is magnesium stearate. Additional pharmaceutical excipients commonly accepted and used are found in, for example, Remington's Pharmaceutical Sciences (Gennaro, A., ed., Mack Pub., 1990).

For purposes of parenteral administration, solutions in suitable oil such as sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art. Methods of preparing various pharmaceutical compositions with a certain amount of active ingredient are known, or will be apparent in light of this disclosure, to those skilled in this art.

The half-life of metadoxine in human serum is very short. Lu Yuan et al. (*Chin. Med. J.* 2007 120(2) 160-168), showed a mean half life of about 0.8 hour. A way of prolonging serum levels of active moiety is by administering the material in a sustained-release formulation. Because metadoxine is freely soluble in water and in various biological fluids, it is difficult to sustain its release and prolong its absorption time. Therefore, it was unexpected that sustained release could be achieved. A control release dosage form of metadoxine or metadoxine derivative may be based on a predetermined gradual release of the active ingredient in the biological fluids, resulting in a sustained action with small fluctuations of the plasma level over a prolonged period of time.

In certain embodiments, the delivery system used by this invention may be administered in controlled release formulations. In certain embodiments, the method of administration will be determined by the attending physician or other person skilled in the art after an evaluation of the subject's condition and requirements. An embodiment of the method of the present invention is to administer the therapeutic compound described herein in a sustained release form. Any controlled or sustained release method known to those of ordinary skill in the art may be used with the compositions and methods of the invention such as those described in Langer, *Science* 249(4976):1527-33 (1990). Such method comprises administering a sustained-release composition, a suppository, or a coated implantable medical device so that a therapeutically effective dose of the composition of the invention is continuously delivered to a subject of such a method. Sustained release may also be achieved using a patch designed and formulated for the purpose. The composition of the invention may be delivered via a capsule which allows sustained-release of the agent over a period of time. Controlled or sustained-release compositions include formulation in lipophilic depots (e.g., fatty acids, waxes, oils). Also comprehended by the invention are particulate compositions coated with polymers (e.g., poloxamers or poloxamines). Sustained release formulae or devices, or any topical formulations, may additionally contain compositions to stabilize the composition or permeate physiological barrier such as skin or mucous membrane. Exemplary additional components may include any physiologically acceptable detergent, or solvent such as, for example, dimethylsulfoxide (DMSO).

In all embodiments of the invention, methods and uses of the invention may employ a composition comprising a salt adduct as defined by the invention formulated as a single dose. Said single dose formulation may be an immediate release formulation, a burst formulation, a prolonged release formulation, a sustained release formulation or any other controlled release formulation known to a person skilled in the art.

In other embodiments of the methods and uses of the invention, a composition comprising a salt adduct defined by the invention may be a combined dosage formulation, wherein different types of formulations are administered to a subject, i.e. any combination of an immediate release formulation, a burst formulation, a prolonged release formulation, a sustained release formulation or any other controlled release formulation known to a person skilled in the art, given either in a single dose or in separate doses given separately, concomitantly or sequentially wherein the gap of time between administration of separate dosages is defined based on the condition and severity of disease or disorder of a subject or the physical condition of said subject.

In some embodiments a composition used by the methods of the invention are formulated as combined dosage forms, wherein at least one dosage from of a sult adduct defined by the invention is in an immediate release form and at least one dosage form of a salt adduct defined by the invention (being the same or different from the salt adduct formulated in the immediate release formulation) is formulated as a controlled (slow and/or sustained) release formulation. In other embodiments the weight ratio of a salt adduct as defined by the invention comprised in said at least one immediate release formulation and at least one controlled release formulation may be 1:1, 1:2, 2:1, 3:2, 2:3, 1:3, 3:1, 4:1, 1:4, 5:2, 2:5, 1:5, 5:1. When employing such combined dosage forms in a method or use of the invention, said at least one immediate release form and at least one controlled release form of a salt adduct defined above, may be administered to a subject separately, concomitantly, sequentially, concurrently, consequetively and so forth. In some embodiments said at least one immediate release form is administered initially. In other embodiments said at least one controlled release formulation is administered initially.

In certain embodiments, the metadoxine or metadoxine derivative in compositions of the invention may be formulated for sustained or controlled release over a period of at least 0.5, 1, 2, 3, 4, 5, 6, 7, 8, 9, 10, 11 or 12 hours. In certain embodiments, the metadoxine or metadoxine derivative in compositions used by the invention may be formulated for sustained or controlled release over a period of about 0.5, 1, 2, 3, 4, 5, 6, 7, 8, 9, 10, 11 or 12 hours. In certain embodiments, the metadoxine or metadoxine derivative in compositions used by the invention may be formulated for sustained or controlled release over a period of between about 0.5 or 1 or 2 or 3 or 4 hours and about 5, 6, 7, 8, 9, 10, 11 or 12 hours. In certain embodiments, the metadoxine or metadoxine derivative in compositions used by the invention may be formulated for sustained or controlled release over a period of between about 5 or 6 or 7 or 8 hours and about 9, 10, 11 or 12 hours.

In certain embodiments, the metadoxine or metadoxine derivative in compositions used by the invention may be in immediate, fast of burst release form.

In certain embodiments, the metadoxine or metadoxine derivative in compositions used by the invention may be formulated to release up to 5, 10, 15, 20, 25, 30, 35, 40, 45, 50, 55, 60, 65, 70, 75, 80, 85, 90, 95, 99, 99.5 or 100% of the total metadoxine or metadoxine derivative in about 0.5, 1, 2, 3, 4, 5, 6, 7 or 8 hours. In certain embodiments, the metadoxine or metadoxine derivative in compositions used by the invention may be formulated to release not less than 5, 10, 15, 20, 25, 30, 35, 40, 45, 50, 55, 60, 65, 70, 75, 80, 85, 90, 95, 99, 99.5 or 100% of the total metadoxine or metadoxine derivative in about 0.5, 1, 2, 3, 4, 5, 6, 7 or 8 hours.

In certain embodiments, the metadoxine or metadoxine derivative in compositions used by the invention may be in a combination of sustained or slow release and immediate or fast release forms. In certain embodiments, the relative proportion of sustained or slow release metadoxine or metadoxine derivative to immediate or fast release metadoxine or metadoxine derivative is, e.g., 1 to 99, 5 to 95, 10 to 90, 15 to 85, 20 to 80, 25 to 75, 30 to 70, 35 to 65, 40 to 60, 45 to 55, 50 to 50, 55 to 45, 60 to 40, 65 to 35, 70 to 30, 75 to 25, 80 to 20, 85 to 15, 90 to 10, 95 to 5, or 99 to 1.

In certain embodiments, a polymeric material is used to sustain or control the release of metadoxine or metadoxine derivative. In certain embodiments, the type of polymeric material and the amount of which is used, has a strong influence on the rate of release of metadoxine or metadoxine derivative from the product of the present invention.

Examples of polymers include both hydrophobic and hydrophilic polymers. Examples of hydrophobic polymers include, but are not limited to, ethyl cellulose and other cellulose derivatives, fats such as glycerol palmito-stereate, beeswax, glycowax, castorwax, carnaubawax, glycerol monostereate or stearyl alcohol, hydrophobic polyacrylamide derivatives and hydrophobic methacrylic acid derivatives, as well as mixtures of these polymers. Hydrophilic polymers include, but are not limited to, hydrophilic cellulose derivatives such as methyl cellulose, hydroxypropylmethyl cellulose, hydroxyethylcellulose, hydroxypropyl cellulose, carboxymethyl cellulose, sodium carboxymethylcellulose and hydroxyethyl methyl-cellulose polyvinyl alcohol, polyethylene, polypropylene, polystyrene, polyacrylamide, ethylene vinyl acetate copolymer, polyacrylate, poly-urethane, polyvinylpyrrolidone, polymethylmethacrylate, polyvinyl acetate, polyhydroxyethyl methacrylate, as well as mixtures of these polymers. Furthermore, any mixture of one or more hydrophobic polymer and one or more hydrophilic polymer could optionally be used.

In certain embodiment, a polymeric material to be used in compositions of or used by the invention is microcrystalline cellulose such as "AVICEL PH 101®" manufactured by FMC BioPolymer's.

In certain embodiments, a polymeric material to be used in compositions of or used by the invention is hydroxypropyl methyl-cellulose such as "METHOLOSE®" produced by Shin-Etsu Chemical Co.

In certain embodiments, a polymeric material to be used in compositions of or used by the invention is ethyl cellulose such as "ETHOCEL®", manufactured by The Dow Chemical Company.

In certain embodiments, a polymeric material to be used in compositions of or used by the invention is an acrylic polymer such as "EUDRAGIT RS®", produced by Rohm GmbH.

In certain embodiments, a polymeric material to be used in compositions of or used by the invention is a colloidal silicone dioxide such as "AEROSIL®", manufactured by Degussa.

In certain embodiments, a polymeric material to be used in compositions of or used by the invention is a poly (vinyl acetate) such as "KOLLICOAT® SR", manufactured by BASF.

In certain embodiments, a polymeric material to be used in compositions of or used by the invention is an ethyl acetate and vinyl acetate solution such as "DUROTAK®", manufactured by Delasco Dermatologic Lab & Supply, Inc.

In certain embodiments, the composition of or used by the invention comprises or consists essentially of Formula 1. Formula 1 comprises or consists essentially of 100-3000 mg metadoxine or metadoxine derivative and 5-20,000 mg METHOLOSE®.

In certain embodiments, the composition of or used by the invention comprises or consists essentially of Formula 2. Formula 2 comprises or consists essentially of 100-3000 mg metadoxine or metadoxine derivative and 5-7000 mg ETHOCEL E10®.

In certain embodiments, the composition of or used by the invention comprises or consists essentially of Formula 3. Formula 3 comprises or consists essentially of 100-3000 mg metadoxine or metadoxine derivative and 5-20,000 mg EUDRAGIT RS®.

In certain embodiments, the compositions of or used by the invention comprise or consist essentially of about 250, 300, 400, 500, 600, 700, 800, or 900 mg to about 1000, 1500, 2000, 2500 or 3000 mg metadoxine or metadoxine derivative. In certain embodiments, the compositions of the invention comprise or consist essentially of about 5, 100, 500, or 1000 mg to about 2000, 4000, 10,000, 15,000, or 20,000 mg AVICEL PH 101®. In certain embodiments, the compositions of or used by the invention comprise or consists essentially of about 25, 50, 100, 150, 200, 250, 300, 350, 400, 450, 500, 550 or 600 mg to about 650, 700, 750, 800, 850, 900, 950, 1000, 5000, 10,000, 15,000 or 20,000 mg of a polymeric material. In certain embodiments, the polymeric material is METHOLOSE®, ETHOCEL E10® or EUDRAGIT RS®. In certain embodiments, METHOLOSE® comprises or consists essentially of between 1 and 90% of the formulation, preferably between 5 and 70%. In certain embodiments, ETHOCEL® comprises or consists essentially of between 1 and 30% of the formulation, preferably between 2 and 20%. In certain embodiments, EUDRAGIT® comprises or consists essentially of between 1 and 90% of the formulation, preferably between 5 and 70%.

In certain embodiments, delivery systems of or used by the invention comprise delivery devices. In certain embodiments, the compositions of or used by the invention are delivered by an osmotic process at a controlled rate such as by an osmotic pump. The system may be constructed by coating an osmotically active agent with a rate controlling semipermeable membrane. This membrane may contain an orifice of critical size through which agent is delivered. The dosage form after coming into contact with aqueous fluids, imbibes water at a rate determined by the fluid permeability of the membrane and osmotic pressure of the core formulation. This osmotic imbibition of water results in formation of a saturated solution of active material within the core, which is dispensed at controlled rate from the delivery orifice in the membrane.

In certain embodiments, the compositions of or used by the invention are delivered using biodegradable microparticles. In certain embodiments, the system to prepare microparticles consists of an organic phase comprised of a volatile solvent with dissolved polymer and the material to be encapsulated, emulsified in an aqueous phase. In certain embodiments, the biodegradable polymers that can be used for the microparticle matrix, comprises polylactic acid (PLA) or the copolymer of lactic and glycolic acid (PLAGA). The PLAGA polymer degrades hydrolytically over time to its monomeric components, which are readily removed from the body through natural metabolism.

The preparation of or used by the present invention may also contain an absorption enhancer and other optional components. Examples of absorption enhancers include, but are not limited to, cyclodextrins, phospholipids, chitosan, DMSO, TWEEN®, Brij, glycocholate, saponin, fusidate and energy based enhancing absorption equipment.

Optional components present in the dosage forms include, but are not limited to, diluents, binders, lubricants, surfactants, coloring agents, flavors, buffering agents, preservatives, stabilizing agents and the like.

Diluents, also termed "fillers" include, for example, dicalcium phosphate dihydrate, calcium sulfate, lactose, cellulose, kaolin, mannitol, sodium chloride, dry starch, hydrolyzed starches, silicon dioxide, colloidal silica, titanium oxide, alumina, talc, microcrystalline cellulose, and powdered sugar. For administration in liquid form, the diluents include, for example, ethanol, sorbitol, glycerol, water and the like.

Binders are used to impart cohesive qualities to the formulation. Suitable binder materials include, but are not limited to, starch (including corn starch and pregelatinzed starch), gelatin, sugars (including sucrose, glucose, dextrose, lactose and sorbitol), polyethylene glycol, waxes, natural and synthetic gums, e.g., acacia, tragacanth, sodium alginate, celluloses, and Veegum, and synthetic polymers such as polymethacrylates and polyvinylpyrrolidone.

Lubricants are used to facilitate manufacture; examples of suitable lubricants include, for example, magnesium stearate, calcium stearate, stearic acid, glyceryl behenate, and polyethylene glycol.

Surfactants may be anionic, cationic, amphoteric or nonionic surface active agents, with anionic surfactants preferred. Suitable anionic surfactants include, but are not limited to, those containing carboxylate, sulfonate and sulfate ions, associated with cations such as sodium, potassium and ammonium ions. Particularly preferred surfactants include, but are not limited to long alkyl chain sulfonates and alkyl aryl sulfonates such as sodium dodecylbenzene sulfonate; dialkyl sodium sulfosuccinates, such as sodium bis-(2-ethylhexyl)-sulfosuccinate; and alkyl sulfates such as sodium lauryl sulfate.

Stabilizing agents such as antioxidants, include, but are not limited to, propyl gallate, sodium ascorbate, citric acid, calcium metabisulphite, hydroquinone, and 7-hydroxycoumarin.

If desired, the compositions of or used by the invention may also contain minor amounts of nontoxic auxiliary substances such as wetting or emulsifying agents, preservatives, and the like.

Any of the compositions of or used by the invention may be used alone or in combination with one or more additional therapeutic agents, for the improvement of cognitive behavior. Examples of additional therapeutic agents are: amphetamines, methylphenidate HCl, dexmethylphenidate hydrochloride, atomoxetine, reboxetine, fluoxatine, sertraline, paroxetine, fluoroxamine, citalopram, venlafaxine, bupropion, nefazodone and mirtazapine.

The amount of both the compound and the additional therapeutic agent that may be combined with the carrier materials to produce a single dosage form will vary depending upon the host treated and the particular mode of administration. Preferably, the compositions of this invention should be formulated so that a dosage of between 0.1-1 g/kg body weight/day, preferably 0.1-300 mg/kg body weight, can be administered. The dose of the compound depends on the condition and the illness of the patient, and the desired daily dose. In human therapy, the oral daily dose is preferably 10-3000 mg. These doses are administered in unit dosage forms, which may be divided into 2-3 smaller doses for each day in certain cases, especially in oral treatment. In certain embodiments, the compositions of the present invention may act synergistically in combination with each other and may further act synergistically in the presence of an additional therapeutic agent. Therefore, the amount of compound(s) and additional therapeutic agent(s) in such compositions will be less than that required in a monotherapy utilizing only that therapeutic agent. In such compositions a dosage of between 0.1-1 g/kg bodyweight/day of the additional therapeutic agent can be administered.

Use of Metadoxine or Metadoxine Derivative to Prepare Therapeutic Compositions

In certain embodiments, the present invention provides a use of metadoxine or metadoxine derivative (including a functional, physiologically acceptable derivative of metadoxine) in the manufacture of a therapeutic composition useful for administering to a subject for improvement of cognitive function or treatment and/or prevention of cognitive disorders or malfunction according to any one of the methods of the invention as described herein.

EXAMPLES

The following examples are intended to be illustrative of the disclosed invention. The examples are non-limiting, and the skilled artisan will recognize that other embodiments are within the scope of the present invention. Where not otherwise noted, methods were performed using techniques that would be understood by one of ordinary skill in the art.

Example 1

Metadoxine Release from Various Formulations

Metadoxine was formulated at various ratios of immediate release and slow release according to Table 1:

TABLE 2

| | Metadoxine formulations | | | |
|---|---|---|---|---|
| Formulation No. | Dosage | % Immediate Release | % Slow Release | No. of tested patients |
| 1 | 700 mg | 30 | 70 | 3 |
| 2 | 1400 mg | 30 | 70 | 3 |
| 3 | 1190 mg | 60 | 40 | 6 |
| 4 | 2100 mg | 30 | 70 | 6 |

The above mentioned formulations were given to fasted healthy patients. Blood samples were collected following a predetermined time schedule in order to characterize formulation adsorption and elimination.

FIG. 1 shows that Metadoxine reaches maximal concentration immediately after about 0.5 hour and may remain in the blood for up to about 7 hours. After single administration in healthy Caucasian subjects, dose-linearity was demonstrated for $C_{max}$ and AUC over the dose range of 700 to 2100 mg.

TABLE 3

Mean Pharmacokinetic Parameters of Metadoxine 700 mg, 1400 mg and 2100 mg after a Single Administration to Healthy Caucasian Adults

| Pharmacokinetic Parameter | Dual Extended Release Formulation of Metadoxine | | |
|---|---|---|---|
| | 700 mg | 1400 mg | 2100 mg |
| $C_{max}$ (ng/mL) | 4.8 (4.5-6.3) | 11.2 (8.0-12.8) | 17.7 (15.2-22.3) |
| $AUC_{0-\infty}$ (ng·h/mL) | 8.29 (8.02-8.44) | 54.49 (41.18-69.42) | 75.74 (56.99-98.34) |
| $t_{1/2}$ (h) | 1.00 (0.81-1.30) | 1.40 (0.82-1.78) | 1.22 (1.02-1.53) |

Example 2

Metadoxine Formulation for Improvement of Cognitive Performance of ADHD/ADD Patients 38 ADHD/ADD adult patients (age 18-45) of ADHD unit of the Geha Mental Health Center (Israel) were tested.

A total of four tablets were administered to each patient:

Two tablets of immediate release (IR) formulation (defined in Table 4) and

Two tablets of slow release (SR) formulation (defined in Table 5).

The total dose of metadoxine administered was 1400 mg, in dual (combined immediate and slow) release formulation.

TABLE 4

Parameters of IR Drug Product Batch

| | |
|---|---|
| Strength | 245 mg Metadoxine |
| Appearance | Concave round off-white tablets |
| Diameter | 8 mm |
| Dissolution | >75% in 45 min |
| Excipients | Polyvinylpyrrolidone (PVP), Cellulose, Silicone Dioxide, Magnesium Stearate |
| % excipients of total | 30% |

TABLE 5

Parameters of SR Drug Product

| | |
|---|---|
| Strength | 455 mg Metadoxine |
| Appearance | Concave round off-white tablets |
| Diameter | 11.5 mm |
| Dissolution | 82.8% in 8 hours |
| Excipients | Ethyl Cellulose (EC), Hydroxypropylmethylcellulose (HPMC), Silicone Dioxide, Magnesium Stearate |
| % excipients of total | 15% |

Tests at inclusion included selection of patients, and included clinical diagnosis by DSM IV, psychiatric examination, WURS & ASRS questionnaires, TOVA (Test of Variables of Attention) score, Wechsler (Wechsler Adult Intelligence Scale) subtests, BDI (Beck Depression Inventory) and STAI (State-Trait Anxiety Inventory) questionnaire. More than one week after the inclusion, the participants were given a single dose of Metadoxine SR (1400 mg) and after 90 minutes performed again the Wechsler subtests and the TOVA test.

The TOVA is a computerized test developed to assess attention and impulsivity in normal and clinical populations. Main outcome measures for the TOVA are the Omission Standard Score (SS; inattention measure) the Commission Standard Score (SS; measure of impulse control), the Response Time (RT) SS, the Variability in RT SS, and overall ADHD SS (a composite score of the previous submeasures).

The Primary outcome measure was the ADHD Score, TOVA Omission, TOVA Commission, TOVA RT and TOVA Variability analysed as Standard Score in % compared to the patient's prior performance of the TOVA test at baseline. Secondary outcome measures were Subtests from Weschler: Digit span, Symbol Search, Digit symbol.

Results:

TABLE 6

Results of TOVA
(Test of Variables of Attention Continuous Performance Test)

| | Baseline | Post-medication |
|---|---|---|
| ADHD Score (n = 34)* | | |
| Mean | −5.18 [−25.30 +4.29] | −1.77 [−13.9 +6.29] |
| Δ (% of improvement vs Baseline) | Δ = +3.41 (+65.8%) | |
| p-value | p < 0.001 | |
| Omission Score (n = 38) | | |
| Mean | 77.45 [40 109] | 90.34 [40 109] |
| Δ (% of improvement vs Baseline) | Δ = +12.89 (+16.6%) | |

TABLE 6-continued

Results of TOVA
(Test of Variables of Attention Continuous Performance Test)

| | Baseline | Post-medication |
|---|---|---|
| p-value | p < 0.03 | |
| Commission Score (n = 38) | | |
| Mean | 98.16 [40 121] | 105.11 [48 123] |
| Δ (% of improvement vs Baseline) | Δ = +6.95 (+7.1%) | |
| p-value | p < 0.01 | |
| RT Time (n = 38) | | |
| Mean | 88.87 [40 131] | 99.89 [45 135] |
| Δ (% of improvement vs Baseline) | Δ = +11.02 (+12.4%) | |
| p-value | p < 0.02 | |
| RT Var (n = 38) | | |
| Mean | 62.42 [40 123] | 86.5 [40 137] |
| Δ (% of improvement vs Baseline) | Δ = +24.18 (+38.6%) | |
| p-value | p < 0.001 | |

*Norms: ADHD Score >−1.8, Omission, Commission, Response Time and Variability Scores: 85-115

TOVA tests (results shown in Table 6) were performed at baseline and post-medication. The results of the TOVA test indicate statistically significant improvement in all TOVA parameters, those related to inattention (number of omissions, greater stability in Response Time and decrease in overall ADHD score) and those related to impulsivity (number of commissions).

TABLE 7

Results of Wechsler subtests

| | Baseline | Post-medication |
|---|---|---|
| Correct Symbols (n = 38) | | |
| Mean | 34.53 [18 59] | 37.92 [22 57] |
| Δ (improvement vs Baseline) | Δ = +3.39 | |
| p-value | p < 0.002 | |
| Symbol Search (n = 38) | | |
| Mean | 74.60 [54 119] | 81.76 [61 112] |
| Δ (improvement vs Baseline) | Δ = +7.16 | |
| p-value | p < 0.001 | |
| Digits forwards (n = 38) | | |
| Mean | 10.00 [5 14] | 10.71 [7 14] |
| Δ (improvement vs Baseline) | Δ = +0.71 | |
| p-value | p < 0.03 | |
| Digits backwards (n = 38) | | |
| Mean | 6.97 [3 13] | 7.84 [2 14] |
| Δ (improvement vs Baseline) | Δ = +0.87 | |
| p-value | p < 0.01 | |
| Total Digit (n = 38) | | |
| Mean | 16.97 [9 26] | 18.55 [10 27] |
| Δ (improvement vs Baseline) | Δ = +1.58 | |
| p-value | p < 0.002 | |

Wechsler tests (results shown in Table 7) were performed at baseline and post-medication. The results of the Wechsler subtests confirmed the ability of Metadoxine to improve cognitive functions in the ADHD Adult population.

Discussion:

The comparison of the results for the overall ADHD score obtained with Metadoxine SR formulation of the invention with baseline scores, given in Table 8 below, shows an improvement in ADHD Standard Score of about +90% versus baseline.

TABLE 8

Comparisons of ADHD Score
(patients treated with Metadoxine)

| Comparison<br>(1) Baseline<br>(3) Metadoxine<br>1400 mg<br>n = 12 | Mean Difference | Std Error | p value[1] | 95% Confidence Interval | |
|---|---|---|---|---|---|
| (3) | −4.417* | 1.283 | 0.026 | −8.28 | −0.55 |
| (1) | +8.103* | 1.866 | 0.007 | 2.48 | 13.73 |
| (3) | +3.687 NS | 1.883 | 0.258 | −1.99 | 9.37 |
| (1) | +4.417* | 1.866 | 0.026 | 0.55 | 8.28 |

*the mean difference is significant at the 0.05 level
[1]adjustment for multiple comparisons: Bonferroni Example 3

Metadoxine Formulation for Improvement of Cognitive Performance of ADHD/ADD Patients Ten adult ADHD subjects patients (age 18-45) of ADHD unit of the Geha Mental Health Center (Israel) were tested.

A single tablet was administered to each patient comprising 1400 mg dose of DER Metadoxine.

The total dose of metadoxine administered was 1400 mg, in dual extended release formulation.

Tests at inclusion included selection of patients, and included clinical diagnosis by DSM IV, psychiatric examination, WURS & ASRS questionnaires, TOVA (Test of Variables of Attention) score, Wechsler (Wechsler Adult Intelligence Scale) subtests, BDI (Beck Depression Inventory) and STAI (State-Trait Anxiety Inventory) questionnaire.

After the inclusion, the participants were given a single dose of Metadoxine DER (1400 mg) and performed the TOVA test after the following time periods: 90 minutes, 4 hours and 7 hours.

The TOVA is a computerized test developed to assess attention and impulsivity in normal and clinical populations. Main outcome measures for the TOVA are the Omission Standard Score (SS; inattention measure) the Commission Standard Score (SS; measure of impulse control), the Response Time (RT) SS, the Variability in RT SS, and overall ADHD SS (a composite score of the previous submeasures).

The Primary outcome measure was the ADHD Score, TOVA Omission, TOVA Commission, TOVA RT and TOVA Variability analysed as Standard Score in % compared to the patient's prior performance of the TOVA test at baseline. Secondary outcome measures were Subtests from Weschler: Digit span, Symbol Search, Digit symbol.

Results and Discussion:

As can be seen from Table 9, a significant improvement is manifested in the ADHD score, RT Time and RT variability (which are considered to be more sensitive parameters in the adult population), at all-time points after baseline, with 4 hrs showing the maximal outcome. It is noted that commission results showed improvement even after 90 minutes after dosing. It is further noted that although after 7 hrs after dosing, improvement was diminished, even 7 hrs after dosing showed improved results compared to baseline.

TABLE 9

| | Baseline | 90 min | 4 hr | 7 hr |
|---|---|---|---|---|
| ADHD Score | −3.79 | −0.34 | 0.85 | 0.04 |
| Omission | 91.8 | 84.3 | 93.3 | 88.1 |
| Commission | 108.2 | 103.6 | 98.6 | 102.4 |
| RT Time | 92.3 | 110 | 113.1 | 112.3 |
| RT Variability | 92.625 | 101.9 | 106 | 100.2 |

Example 4

Effects of Metadoxine on Cognitive Performance of Sleep Deprived Subjects

The double-blind study compared the cognitive performance of 14 healthy adults (ages 18-40) using cognitive tasks following a 24-hour period of total sleep deprivation (TSD).

Standardized neuropsychological testing was conducted in cognitive domains which have previously been shown to be affected by sleep and/or sleep deprivation, such as processing speed, attention, and inhibition.

All participants wore an actigraph for one week prior to study onset and for the duration of the study to document sleep-wake behavior.

Each participant was administered with one of two counterbalanced treatment conditions: (1) Composition of the invention (single dose 1400 mg DER Metadoxine) or (2) Placebo.

Procedures a. Sleep Protocols:

On the day of the study, participants were instructed to:
1. Wake up no later than 08:00 (at home).
2. Not to nap for the duration of the day and refrain from any alcohol or stimulant use.
3. Arrive at the sleep laboratory at 20:00.
4. Remain awake for the duration of the night (with supervision).
5. Refrain from consumption of any food or liquids starting at 05:00.
6. At 07:00 the following morning, participants received either a composition of the invention or placebo from the study physician or licensed nurse dedicated to the study.
7. Participant performed cognitive tasks at 08:30 (task duration: 30 minutes).

b. Actigraphy.

An actigraph is a small, light device (~size of a wrist watch), placed on the subject's non-dominant wrist, which contains a movement sensor (accelerometer) that collects physical movement data sampled several times per second and stored in 1-minute epochs. Sleep/wake patterns were monitored using actigraphy, which has been validated against polysomnography, resulting in high correlations on sleep measures. Participants continuously wear an actigraph starting one week before the experimental phase until the end of the active protocol. Actigraphs are waterproof and durable and attached using non-removable wristbands, to ensure they are worn continuously.

c. Neuropsychological Testing.

Digit Symbol Substitution Test (DSST) (WAIS-III) is a paper-and-pencil processing speed task that measures visual-motor coordination and processing speed. It consists of nine digit-symbol pairs followed by a list of digits. Under each digit the subject is asked to write down the corresponding symbol as quickly as possible. The number of correct symbols within the allowed time (120 seconds) is measured.

Connors' Continuous Performance Task (CPT; www.bdikalkeshev.co.il (Tel-Aviv University)) is a computerized task that covers cognitive domains reported to be affected by sleep or sleep loss, including processing speed, attention, and inhibition. Different figures are flashed sequentially on a computer screen and participants are instructed to respond to certain figures as quickly as possible (using keyboard), while inhibiting other figures (i.e., not responding). This task takes approximately 17 minutes to complete.

Digit Span (WA IS-III) is a test of attention, concentration, and working memory. Subjects are given sets of digits to repeat initially forwards then backwards. The task takes approximately 5 minutes to complete.

Paced Auditory Serial Addition Task—3rd Edition (PASAT-III) is a computerized task that measures auditory information processing speed and flexibility, as well as working memory. Single digits are presented either every 3 seconds (trial 1) or every 2 seconds (trial 2), and the patient must add each new digit to the one immediately prior to it. The PASAT is presented on compact disk to control the rate of stimulus presentation. The test score is the total number of correct sums given (out of 60 possible) in each trial. This task takes approximately 8 minutes to complete.

The tests were performed by a trained staff and took approximately 45 minutes to complete.

At the end of each cognitive testing session, the Karolinska Sleepiness Scale (KSS: 9-point anchored scale) was administered, together with a series of 10-point Likert scales asking about motivation to perform well, ability to concentrate, amount of effort required to perform the task, and perceived task difficulty. The Likert questions are useful in examining whether performance is related to subjective effort, task difficulty, or sleepiness.

Results and Discussion

Results show clear trends of the efficacy of DER Metadoxine treatment over placebo treatment. Table 10 shows the significance of the difference (delta) between Placebo and Drug outcomes:

TABLE 10

| N | Mean | Std. Dev. | Minimum | Median | Maximum | $p > |t|$ |
|---|------|-----------|---------|--------|---------|-----------|
| CPT Omission (Raw Score) | | | | | | |
| 14 | 3.86 | 9.18 | −2.00 | 0.00 | 34.00 | 0.07 |
| CPT Reaction Time Standard Deviation | | | | | | |
| 14 | 1.64 | 3.91 | −3.01 | 0.20 | 12.10 | 0.07 |
| CPT Variability | | | | | | |
| 14 | 6.41 | 13.64 | −4.37 | 0.48 | 43.52 | 0.05 |

Example 5

Metadoxine Formulation for Improvement of Cognitive Performance of Elderly Subjects Twenty five patients of 60-79 years suffering from mild cognitive impairment (MCI) perform computerized neuropsychological test (Mindstreams) at the beginning of the study—(control 1), following 1 week administration of 350 mg metadoxine formulation twice a day (test 1), following 1 week wash-out period (control 2) and following 1 week administration of placebo formulation (test 2).

The results are analyzed for differences between control and test. An improvement in some parameters like: digit recall, pattern recall with drug compared to placebo is expected.

Example 6

Metadoxine Formulation for Improvement of Cognitive Performance of Tired Subjects Twenty physicians, following 30 hours without any sleep, perform Ray's memory test at the beginning of the study-control (baseline of study) and 1 hour after administration of metadoxine formulation-test.

The results are analyzed for differences between control and test. An improvement in some parameters like: number of remembered words with drug is expected in the treated group compared to control.

Example 7

Metadoxine Formulation for Improvement of Cognitive Performance of Alzheimer's Disease (AD) Patients Twenty AD patients perform memory test at the beginning of the study-control (baseline of study) and after 1 month administration of metadoxine formulation. The results are analyzed for differences between control and test. An improvement in some parameters like: digit recall with drug compared to control is expected.

Example 8

Metadoxine Formulation for Improvement of Cognitive Performance of Multiple Sclerosis Disease (MS) Patients Twenty MS patients perform memory test at the beginning of the study-control (baseline of study) and after 1 month administration of metadoxine formulation. The results are analyzed for differences between control and test. An improvement in some parameters like: digit recall with drug compared to control is expected.

Example 9

Metadoxine Formulation for Treatment of SWSD (Shift Work Sleep Disorder)

Sixty volunteers with chronic SWSD are divided into two groups: volunteers of one receive Metadoxine 700 mg SR capsules, and those of the second group receive placebo capsules. Both groups are tested for: Psychomotor Vigilance Task (10 minute visual sustained-attention test that is sensitive to sleepiness), Continuous Performance test (CPT-14 minutes computer vigilance task) and Simulated Driving Task (20 minutes driving task sensitive to sleepiness which runs on a computer with software, steering wheel, accelerator and brake). Tests are performed at baseline and after treatment.

The results of measured parameters like: reaction time, commissions, omissions, lane variability, and speed variability are analyzed. Better results are expected for the group receiving Metadoxine.

Example 10

Comparative Dissolution Test: Immediate Release Vs. Slow Release

Immediate release tablets were prepared using high shear wet granulation technology according to the following composition:

| | |
|---|---|
| Metadoxine | 500 milligrams |
| AVICEL PH 101 ® | 72 milligrams |
| PVK K-30 | 28 milligrams |
| Magnesium stearate | 5 milligrams |

Slow release tablets were prepared using high shear wet granulation technology according to the following composition:

| | |
|---|---|
| Metadoxine | 455 milligrams |
| METHOLOSE ® 90SH | 152 milligrams |
| ETHOCEL E10 ® | 25 milligrams |
| AEROSIL 200 ® | 5 milligrams |
| Magnesium stearate | 7 milligrams |

Figure 2:
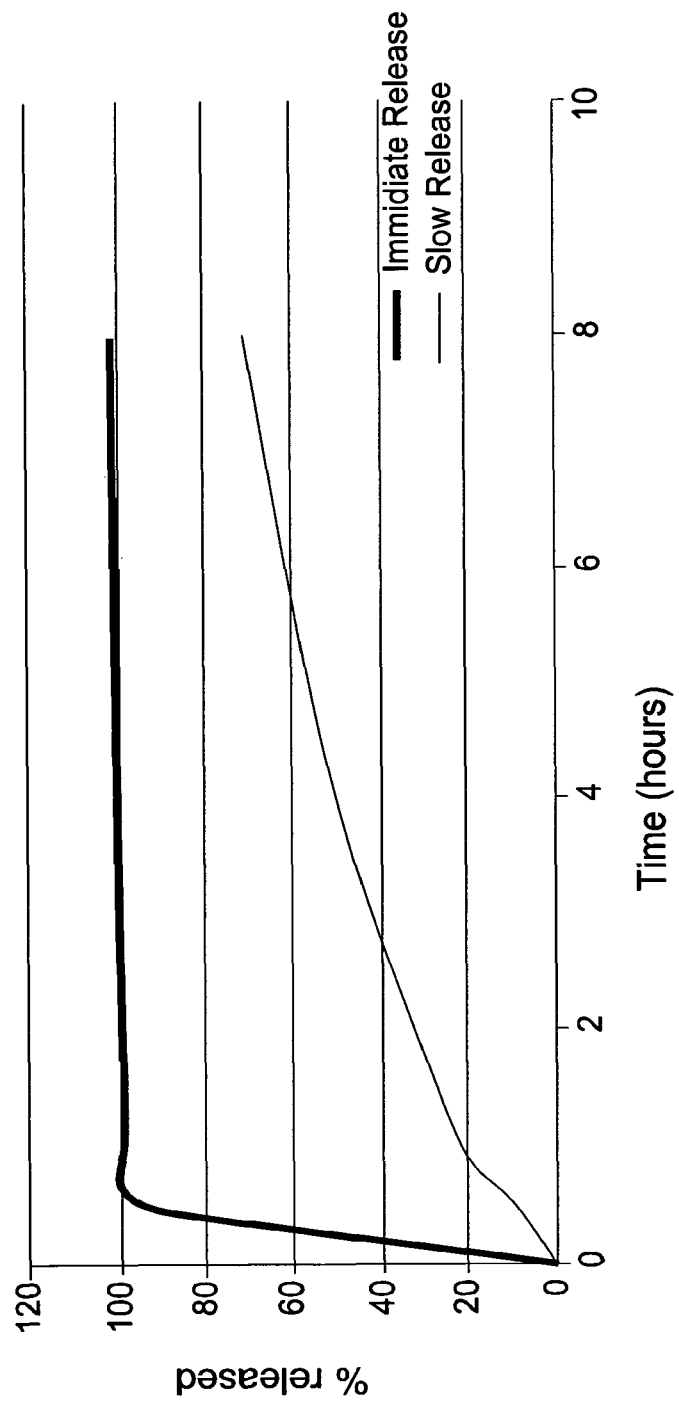
FIG. 2 illustrates the rates of release of immediate-release formulation compared to release from slow-release tablets. Metadoxine (%) released vs. time (hours).

Dissolution was tested using USP Apparatus 2 (paddles), 50×rpm, in 500 ml intestinal fluid pH=6.8, 37° C. Comparative dissolution results are presented in FIG. 2. The immediate release formulation released more than 90% in 0.5 hour, while slow release tablets released about 70% over 8 hours.

Example 11

Slow Release Capsules of Metadoxine

Granules were prepared using high shear granulation and vacuum drying. This is an example of an acrylic hydrophobic polymer as a polymeric material.

| | |
|---|---|
| Metadoxine | 350 milligrams per capsule |
| Calcium carbonate | 45 milligrams per capsule |
| EUDRAGIT RS ® | 60 milligrams per capsule |

Materials were mixed together and granulated with a EUDRAGIT RS® solution in ethanol. Granules were filled into gelatin capsules.

Example 12

Controlled Release Syrup of Metadoxine

Syrup is prepared using an overhead rotary mixer.

| | |
|---|---|
| Metadoxine granules | 700 milligrams per 5 milliliters |
| Cherry flavor | 10 milligrams per 5 milliliters |
| Xylitol solution | ad. 5 milliliters volume |

Metadoxine slow release granules (from Example 8) are mixed in xylitol solution. Cherry flavor is added.

Example 13

Ready-to-Swallow Sachets of Metadoxine

Two granulations are performed in a mixture granulator:

| | |
|---|---|
| Granules No. 1: | |
| Metadoxine | 500 milligrams |
| PVP K-25 | 10 milligrams |
| Granules No. 2: | |
| Metadoxine | 800 milligrams |
| METHOLOSE ® 90SH | 200 milligrams |
| ETHOCEL E10 ® | 50 milligrams |
| Final Mix: | |
| Magnesium stearate | 10 milligrams |
| AEROSIL 200 ® | 5 milligrams |
| Strawberry flavor | 10 milligrams |

Granules No 1 (immediate absorption formula) and Granules No 2 (slow release formula) are mixed together with other ingredients and filled into sachets.

Example 14

Dermal Patch of Metadoxine

Materials (below) are mixed together to form a clear gel. The gel is coated onto a backing membrane by using coating equipment. The laminate is dried and a polyester release liner is laminated onto the dried metadoxine gel. The sheet is cut into patches and stored in a cool place.

| | |
|---|---|
| Metadoxine | 2500 milligrams |
| DUROTAK ® 387-2287 | 200 milligrams |
| Ethanol | 10 milliliters |
| Water | 5 milliliters |

Example 15

Metadoxine Effervescent Powder

Micro granules (pellets) are prepared using extrusion technology:

| | |
|---|---|
| Metadoxine | 100 milligrams |
| METHOLOSE ® 90 SH | 35 milligrams |
| Pellets are mixed with | |
| Metadoxine | 200 milligrams |
| Sodium bicarbonate | 60 milligrams |
| Citric acid | 100 milligrams |
| Sucralose | 20 milligrams |
| Cherry flavor | 10 milligrams |

The mixture is filled into sachets.

We claim:

1. A method for treating a subject with attention deficit/hyperactivity disorder, wherein the subject is not (i) under the influence of alcohol; (ii) an alcoholic; or (iii) an abstinent alcoholic, said method comprising administering a total per day dose of metadoxine of between 700-3000 mg, wherein the metadoxine is formulated as a combination of slow release and immediate release forms, wherein (a) the slow release form provides for sustained release of the metadoxine for at least 8 hours, and (b) the relative proportion of the slow release metadoxine to the immediate release metadoxine is between about 60:40 and 80:20.

2. The method according to claim 1, wherein the relative proportion of the slow release metadoxine to the immediate release metadoxine is about 65:35.

3. The method according to claim 1, wherein the slow release form of metadoxine is formulated with a combination of hydroxypropylmethyl cellulose and ethylcellulose.

4. The method according to claim 1, wherein the immediate release form of metadoxine is formulated with hydroxypropyl cellulose.

5. The method of claim 1, wherein the metadoxine is administered daily, every other day or weekly.

6. The method of claim 1, wherein the metadoxine is administered in one, two, or three dosage forms per day.

* * * * *